US012226109B2

United States Patent
Carusillo

(10) Patent No.: US 12,226,109 B2
(45) Date of Patent: *Feb. 18, 2025

(54) POWERED SURGICAL DRILL HAVING TRANSDUCER ASSEMBLY INCLUDING AT LEAST TWO ROTATION SENSOR DEVICES FOR USE IN DETERMINING BORE DEPTH OF A DRILLED HOLE

(71) Applicant: Stryker Corporation, Kalamazoo, MI (US)

(72) Inventor: Steve Carusillo, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 123 days.

This patent is subject to a terminal disclaimer.

(21) Appl. No.: 18/087,297

(22) Filed: Dec. 22, 2022

(65) Prior Publication Data

US 2023/0130042 A1   Apr. 27, 2023

Related U.S. Application Data

(63) Continuation of application No. 17/052,177, filed as application No. PCT/US2019/030180 on May 1, 2019, now Pat. No. 11,540,841.

(Continued)

(51) Int. Cl.
    *A61B 17/16*     (2006.01)
    *A61B 90/00*     (2016.01)

(52) U.S. Cl.
    CPC ...... *A61B 17/1626* (2013.01); *A61B 17/1624* (2013.01); *A61B 90/06* (2016.02); *A61B 2090/062* (2016.02)

(58) Field of Classification Search
    CPC . A61B 17/16; A61B 17/1613; A61B 17/1615; A61B 17/1617; A61B 17/162;

(Continued)

(56) References Cited

U.S. PATENT DOCUMENTS

| 5,200,747 A | 4/1993 | Betz et al. |
| 5,838,222 A | 11/1998 | Al-Rawi |

(Continued)

FOREIGN PATENT DOCUMENTS

| CA | 2729102 A1 | 12/2009 |
| CA | 2729102 C | 5/2014 |

(Continued)

OTHER PUBLICATIONS

English language abstract and machine-assisted English translation for EP 2 392 899 A2 extracted from espacenet.com database on Nov. 27, 2023, 12 pages.

(Continued)

*Primary Examiner* — Eric S Gibson
(74) *Attorney, Agent, or Firm* — Howard & Howard Attorneys PLLC

(57) ABSTRACT

A surgical drill for drilling a hole in a workpiece includes a housing, a probe moveably mounted to the housing, and a transducer assembly. The transducer assembly includes a gear coupled to the probe and at least two rotational sensor devices coupled to the gear to determine an amount of movement of a probe relative to a housing to determine a bore depth of the hole. The gear has a reference point having an angular path of rotation about a gear axis subdivided into separate first and second arcuate regions. A first sensor device is configured to detect a rotational position of the reference point in the first arcuate region, and a second sensor device is configured to detect a rotational position of the reference point in at least the second arcuate region, with the first sensor device incapable of detecting the reference point in the second arcuate region.

20 Claims, 10 Drawing Sheets

Related U.S. Application Data

(60) Provisional application No. 62/665,024, filed on May 1, 2018.

(58) Field of Classification Search
CPC ............ A61B 17/1624; A61B 17/1626; A61B 17/1628; A61B 90/06
See application file for complete search history.

(56) References Cited

U.S. PATENT DOCUMENTS

| | | | |
|---|---|---|---|
| 6,665,948 B1 * | 12/2003 | Kozin | A61B 90/06 175/45 |
| 8,603,148 B2 | 12/2013 | Raven, III et al. | |
| 8,821,493 B2 * | 9/2014 | Anderson | A61B 17/17 606/171 |
| 8,894,654 B2 * | 11/2014 | Anderson | B25B 21/002 173/176 |
| D719,594 S | 12/2014 | Leugers | |
| D722,627 S | 2/2015 | Leugers | |
| 8,970,207 B2 * | 3/2015 | Baumgartner | A61B 90/06 324/207.2 |
| D727,985 S | 4/2015 | Leugers | |
| D732,364 S | 6/2015 | Rinaldis et al. | |
| 9,138,188 B2 | 9/2015 | McGinley | |
| 9,198,642 B2 * | 12/2015 | Storz | A61B 17/00 |
| 9,204,885 B2 * | 12/2015 | McGinley | A61B 17/162 |
| D759,244 S | 6/2016 | Leugers | |
| D759,245 S | 6/2016 | Leugers | |
| 9,358,016 B2 * | 6/2016 | McGinley | A61B 17/162 |
| 9,370,372 B2 | 6/2016 | McGinley et al. | |
| 9,468,445 B2 | 10/2016 | McGinley et al. | |
| 9,492,181 B2 * | 11/2016 | McGinley | A61B 17/162 |
| 9,526,511 B2 * | 12/2016 | Anderson | A61B 17/1633 |
| 9,554,807 B2 | 1/2017 | McGinley et al. | |
| 9,649,141 B2 | 5/2017 | Raven, III et al. | |
| D791,944 S | 7/2017 | Palazzolo et al. | |
| D793,831 S | 8/2017 | Russell et al. | |
| D793,832 S | 8/2017 | Russell et al. | |
| D793,833 S | 8/2017 | Russell et al. | |
| D794,190 S | 8/2017 | Russell et al. | |
| D794,196 S | 8/2017 | Russell et al. | |
| 9,826,984 B2 | 11/2017 | McGinley et al. | |
| 9,833,244 B2 | 12/2017 | McGinley et al. | |
| 9,833,270 B2 | 12/2017 | Zlotolow | |
| 9,877,734 B2 * | 1/2018 | Anderson | A61B 17/1622 |
| 10,048,145 B2 | 8/2018 | Janik et al. | |
| 10,105,149 B2 * | 10/2018 | Haider | A61B 17/17 |
| 10,149,686 B2 * | 12/2018 | Anderson | A61B 17/1626 |
| 10,159,495 B1 * | 12/2018 | Lambert | A61B 17/1615 |
| 10,321,920 B2 * | 6/2019 | McGinley | A61B 17/1633 |
| 10,695,074 B2 * | 6/2020 | Carusillo | A61B 17/162 |
| 10,925,619 B2 * | 2/2021 | Anderson | B25B 23/0064 |
| 11,000,292 B2 * | 5/2021 | McGinley | A61B 17/1633 |
| 11,317,927 B2 * | 5/2022 | Carusillo | A61B 90/06 |
| 11,540,841 B2 * | 1/2023 | Carusillo | A61B 17/1624 |
| 2005/0116673 A1 * | 6/2005 | Carl | A61B 17/1626 318/432 |
| 2009/0326537 A1 * | 12/2009 | Anderson | A61B 17/17 606/80 |
| 2010/0247513 A1 | 9/2010 | Agee et al. | |
| 2011/0245833 A1 * | 10/2011 | Anderson | A61B 17/1628 606/80 |
| 2012/0203228 A1 | 8/2012 | Raven, III et al. | |
| 2013/0022543 A1 | 1/2013 | McGinley | |
| 2013/0072952 A1 * | 3/2013 | Storz | A61B 17/1628 606/1 |
| 2014/0094804 A1 | 4/2014 | Raven, III et al. | |
| 2014/0371752 A1 * | 12/2014 | Anderson | A61B 17/1633 606/80 |
| 2015/0066030 A1 * | 3/2015 | McGinley | A61B 90/30 606/79 |
| 2015/0066035 A1 * | 3/2015 | McGinley | A61B 17/162 606/80 |
| 2015/0066036 A1 * | 3/2015 | McGinley | A61B 17/162 606/80 |
| 2015/0066037 A1 * | 3/2015 | McGinley | A61B 17/1628 606/80 |
| 2015/0066038 A1 * | 3/2015 | McGinley | A61B 17/1615 606/80 |
| 2015/0080966 A1 * | 3/2015 | Anderson | B25B 23/0064 606/280 |
| 2015/0134010 A1 | 5/2015 | Zlotolow | |
| 2015/0141999 A1 * | 5/2015 | McGinley | A61B 17/142 606/82 |
| 2015/0148805 A1 | 5/2015 | McGinley et al. | |
| 2015/0148806 A1 | 5/2015 | McGinley et al. | |
| 2016/0022374 A1 * | 1/2016 | Haider | A61B 17/142 606/96 |
| 2016/0120553 A1 | 5/2016 | Xie | |
| 2016/0128704 A1 * | 5/2016 | McGinley | A61B 17/17 606/86 R |
| 2017/0007289 A1 | 1/2017 | McGinley et al. | |
| 2017/0128081 A1 * | 5/2017 | McGinley | A61B 17/1695 |
| 2017/0143396 A1 * | 5/2017 | McGinley | A61B 90/06 |
| 2017/0143440 A1 * | 5/2017 | McGinley | A61B 34/20 |
| 2017/0189037 A1 | 7/2017 | McGinley et al. | |
| 2017/0231644 A1 * | 8/2017 | Anderson | A61B 17/1633 606/80 |
| 2017/0245868 A1 | 8/2017 | McGinley et al. | |
| 2017/0296250 A1 | 10/2017 | McGinley et al. | |
| 2018/0000526 A1 * | 1/2018 | O'Neil | A61B 50/20 |
| 2018/0140308 A1 * | 5/2018 | Anderson | B23B 49/02 |
| 2018/0250020 A1 * | 9/2018 | Carusillo | A61B 90/03 |
| 2019/0029697 A1 * | 1/2019 | Anderson | A61B 17/1622 |
| 2019/0247057 A1 * | 8/2019 | Anderson | B23B 45/008 |
| 2019/0254685 A1 * | 8/2019 | McGinley | A61B 17/1633 |
| 2019/0290297 A1 * | 9/2019 | Haider | A61B 34/20 |
| 2021/0052285 A1 * | 2/2021 | Carusillo | A61B 17/1626 |
| 2021/0186524 A1 * | 6/2021 | Carusillo | A61B 17/162 |
| 2023/0130042 A1 * | 4/2023 | Carusillo | A61B 17/1624 606/80 |

FOREIGN PATENT DOCUMENTS

| | | |
|---|---|---|
| CN | 102131469 A | 7/2011 |
| CN | 102131469 B | 7/2013 |
| CN | 104995495 A | 10/2015 |
| DE | 102011111671 A1 | 2/2013 |
| EP | 2392899 A2 | 12/2011 |
| EP | 2303148 B1 | 2/2017 |
| EP | 3199112 A1 | 8/2017 |
| EP | 3041419 B1 | 1/2019 |
| EP | 3065650 B1 | 1/2019 |
| EP | 3046490 B1 | 7/2019 |
| WO | 2009158115 A1 | 12/2009 |
| WO | 2011123703 A1 | 10/2011 |
| WO | 2013012457 A1 | 1/2013 |
| WO | 2015034562 A1 | 3/2015 |
| WO | 2015070159 A1 | 5/2015 |
| WO | 2016036756 A1 | 3/2016 |
| WO | 2017040783 A1 | 3/2017 |
| WO | 2017075044 A1 | 5/2017 |
| WO | 2017075060 A1 | 5/2017 |
| WO | 2017075224 A1 | 5/2017 |
| WO | 2017078754 A1 | 5/2017 |
| WO | 2017139674 A1 | 8/2017 |
| WO | 2017172949 A1 | 10/2017 |

OTHER PUBLICATIONS

English language abstract for CN 102131469 A extracted from espacenet.com database on Nov. 4, 2020, 2 pages.
English language abstract for CN 102131469 B extracted from espacenet.com database on Nov. 4, 2020, 2 pages.
International Search Report for Application No. PCT/US2019/030180 dated Aug. 7, 2019, 4 pages.
Machine-assisted English language abstract and machine-assisted English Language Translation for DE 10 2011 111 671 A1 extracted from espacenet.com database on Dec. 14, 2020, 17 pages.

(56) References Cited

OTHER PUBLICATIONS

English language abstract for CN 104995495 A extracted from espacenet.com database on Jul. 21, 2024, 2 pages.

* cited by examiner

POWERED SURGICAL DRILL HAVING TRANSDUCER ASSEMBLY INCLUDING AT LEAST TWO ROTATION SENSOR DEVICES FOR USE IN DETERMINING BORE DEPTH OF A DRILLED HOLE

CROSS REFERENCED APPLICATION

This application is a continuation application of U.S. National Stage Patent Application Ser. No. 17/052,177, filed on Oct. 31, 2020 of International Patent Application No. PCT/US2019/030180, filed on May 1, 2019, which claims priority to and all advantages of U.S. Provisional Patent Application No. 62/665,024, filed May 1, 2018, the disclosures of which are specifically incorporated by reference.

BACKGROUND OF THE DISCLOSURE

One type of powered surgical tool, or powered surgical system, used in orthopedic surgery is the surgical drill. This type of tool includes a housing that contains a motor. A coupling assembly, also part of the drill, releasably holds a drill bit to the motor so that, upon actuation of the motor, the drill bit rotates. As implied by its name, a surgical drill drills bores in the workpiece, such as tissue, against which the drill bit is applied. One type of surgical procedure in which it is necessary to drill a bore is a trauma procedure to repair a broken bone. In this type of procedure, an elongated rod, sometimes called a nail, is used to hold the fractured sections of the bone together. To hold the nail in place, one or more bores are driven into the bone. These bores are positioned to align with complementary holes formed in the nail. A screw is inserted in each aligned bore and nail hole. The screws hold the nail in the proper position relative to the bone.

In another type of procedure, an implant, or workpiece, known as a plate is secured to the outer surfaces of the fractured sections of a bone to hold the sections together. Screws hold the plate to the separate sections of bone. To fit a screw that holds a plate to bone it is necessary to first drill a bore to receive the screw.

As part of a procedure used to drill a screw-receiving bore in a bone, it is desirable to know the end-to-end depth of the bore. This information allows the surgeon to select the size of a screw that is fitted in the bore hole. If the screw is too short, the screw may not securely hold the nail into which the screw is inserted in place. If the screw is too long, the screw can extend an excessive distance out beyond the bone. If the screw extends an excessive distance beyond the bone, the exposed end of the screw can rub against the surrounding tissue. If this event occurs, the tissue against which the screw rubs can be damaged.

Accordingly, an integral part of many bone bore-forming procedures is the measuring of the depth of the bore.

This measurement is often taken with a depth gauge separate from the drill. This requires the surgeon, after withdrawing the drill bit from the bore, to insert the depth gauge into the bore. Then, based on tactile feedback, the surgeon sets the gauge so the distal end of the gauge only extends to the far opening of the bore. Once these processes are complete, the surgeon reads the gauge to determine the depth of the bore. This measurement is disadvantageous because it is both labor and time intensive, is reliant upon human element to confirm the measured depth, and may increase the risk of infection and increase the exposure of the patient to anesthesia.

The present disclosure addresses some of these issues.

SUMMARY OF THE DISCLOSURE

Figure 1:
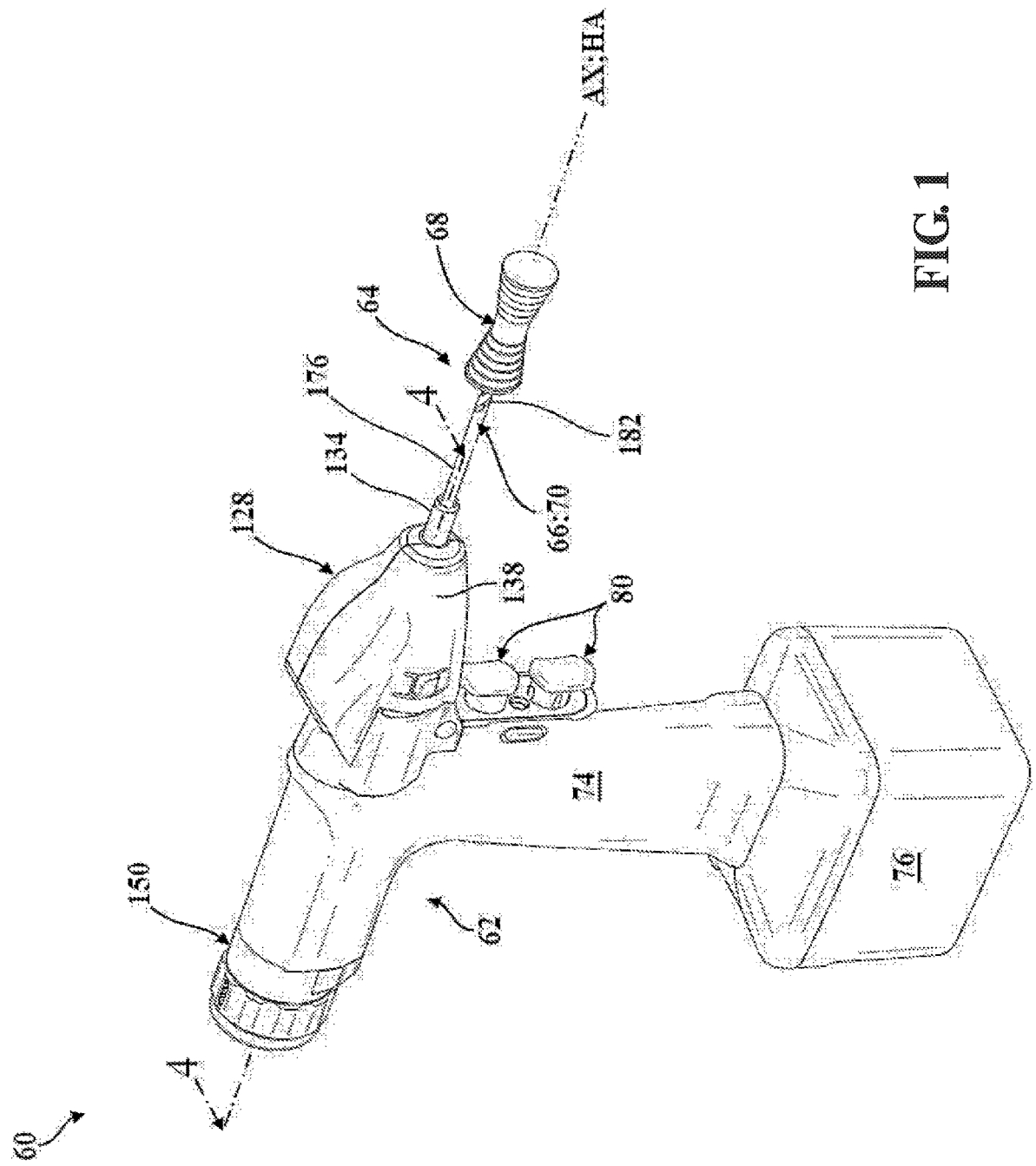
FIG. 1 is perspective view of a surgical system comprising a surgical instrument and end effector assembly, the end effector assembly shown having a drill bit and a tip protector according to one configuration.

A surgical drill for actuating a drill bit is provided. The drill includes a housing, a probe moveably mounted to said housing and adapted for placement against a workpiece, and a transducer assembly. The transducer assembly includes a gear coupled to the probe and configured to rotate more than 360 degrees about a gear axis upon the movement of the probe relative to the housing. The gear having a reference point having an angular path of rotation about the gear axis being divided into a first arcuate region and a second arcuate region. The first arcuate region being separate from the second arcuate region. A transducer comprising at least two potentiometers is also included, with each of the at least two potentiometers coupled to the gear. A first of the at least two potentiometers is configured to detect a rotational position of the reference point in the first arcuate region and a second of the at least two potentiometers is configured to detect the rotational position of the reference point in at least the second arcuate region, the first rotational sensor being incapable of detecting the reference point in the second arcuate region.

A method for determining a bore depth in a workpiece formed by a drill bit attached to a drill is also provided, with the drill including a housing, a probe coupled to the housing, and a transducer assembly including a gear coupled to the probe and a transducer including at least two rotational sensor devices coupled to the gear. The method includes the steps of determining a first rotational position of the gear, determining a number of full rotations of the gear in a single rotational direction about a gear axis from the determined first rotational position, with each of the full rotations corresponding to a predefined amount of movement of the probe relative to the housing. The method also includes determining a second rotational position of the gear, the determined second rotational position the same or different than the determined first rotational position, and determining an amount of movement of the probe relative to the housing from the determined first and second rotational position and from the determined number of full rotations of the gear.

The surgical drill may include a housing, a coupling assembly disposed within the housing adapted to releasably couple the drill bit, a probe moveably mounted to said housing and adapted for placement against tissue. The drill may also include a transducer assembly including a gear coupled to the probe and configured to rotate more than 360 degrees about a gear axis upon the movement of the probe relative to the housing, the gear having a reference point having an angular path of rotation about the gear axis being divided into a first arcuate region and a second arcuate region, the first arcuate region being separate from the second arcuate region. The transducer assembly may also include a transducer comprising at least two rotational sensor devices, each of the at least two rotational sensors fixed rotationally relative to the gear, with the first rotational sensor configured to detect a rotational position of the reference point in the first arcuate region and a second rotational sensor configured to detect the rotational position of the reference point in the second arcuate region. The first rotational sensor being incapable of detecting the reference point in the second arcuate region, with the at least two rotational sensors adapted for independently generating a output signal corresponding to the detected rotational position of the reference point in said respective first and second arcuate region. The drill also includes a controller configured to receive each of the independently generated output signals and, based on each of the independently generated output signals, determine the depth of the bore in the tissue formed by the drill bit.

DETAILED DESCRIPTION

Figure 2:
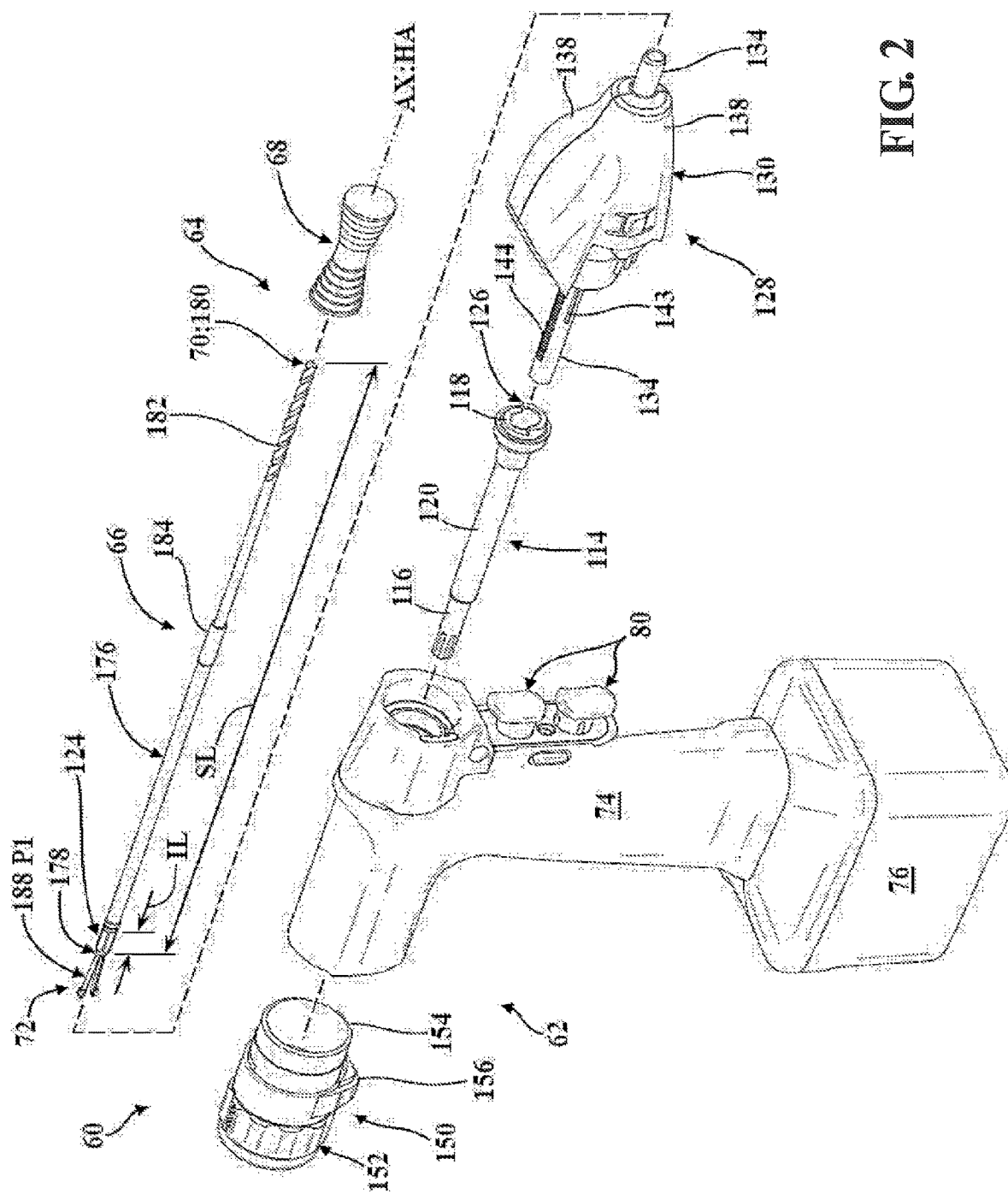
FIG. 2 is a partially-exploded perspective view of the surgical system of FIG. 1, with the surgical instrument shown having a measurement module, a drive assembly, and a release mechanism spaced from a handpiece body, and with the end effector assembly removed from the surgical instrument and shown with the tip protector spaced from a distal cutting tip portion of the drill bit.

With reference to the drawings, where like numerals are used to designate like structure throughout the several views, a surgical system, or surgical drill, is shown at 60 in FIGS. 1-2 for performing an operational function that is typically associated with medical and/or surgical procedures. In the representative configuration illustrated herein, the surgical system 60 is employed to facilitate penetrating a workpiece, such as tissue or bone of a patient. As used herein, unless otherwise indicated, the term workpiece is understood to alternatively refer to tissue and/or bone. To this end, the illustrated configuration of the surgical system 60 comprises a handheld surgical instrument 62 and an end effector assembly, generally indicated at 64. The end effector assembly 64, in turn, comprises a drill bit 66 and may also include a tip protector 68. As is best depicted in FIG. 2, the drill bit 66 extends generally longitudinally along an axis AX between a cutting tip portion, generally indicated at 70, and an insertion portion, generally indicated at 72. The cutting tip portion 70 is configured to engage the workpiece, and the insertion portion 72 is configured to facilitate releasable attachment of the drill bit 66 to the surgical instrument 62.

In order to help facilitate attachment of the drill bit 66 to the surgical instrument 62, in some configurations, the tip protector 68 is configured to releasably secure to the cutting tip portion 70 of the drill bit 66 while concealing at least a portion of the cutting tip portion 70 of the drill bit 66, thereby allowing a user (e.g., a surgeon) of the surgical system 60 to handle and position the drill bit 66 safely during attachment to the surgical instrument 62. Once the end effector assembly 64 has been attached to the surgical instrument 62, the tip protector 68 is subsequently removed from the cutting tip portion 70 of the drill bit 66, and the surgical system 60 can then be utilized to penetrate the workpiece.

Referring now to FIGS. 1-6, in the representative configuration illustrated herein, the surgical instrument 62 is realized as a handheld drill with a pistol-grip shaped handpiece body 74 which releasably attaches to a battery 76 (battery attachment not shown in detail). However, it is contemplated that the handpiece body can have any suitable shape with or without a pistol grip. While the illustrated surgical instrument 62 employs a battery 76 which is releasably attachable to the handpiece body 74 to provide power to the surgical instrument 62 utilized to rotate the drill bit 66, it will be appreciated that the surgical instrument 62 may be configured in other ways, such as with an internal (e.g., non-removable) battery, or with a tethered connection to an external console, power supply, and the like. Other configurations are contemplated.

Figure 3:
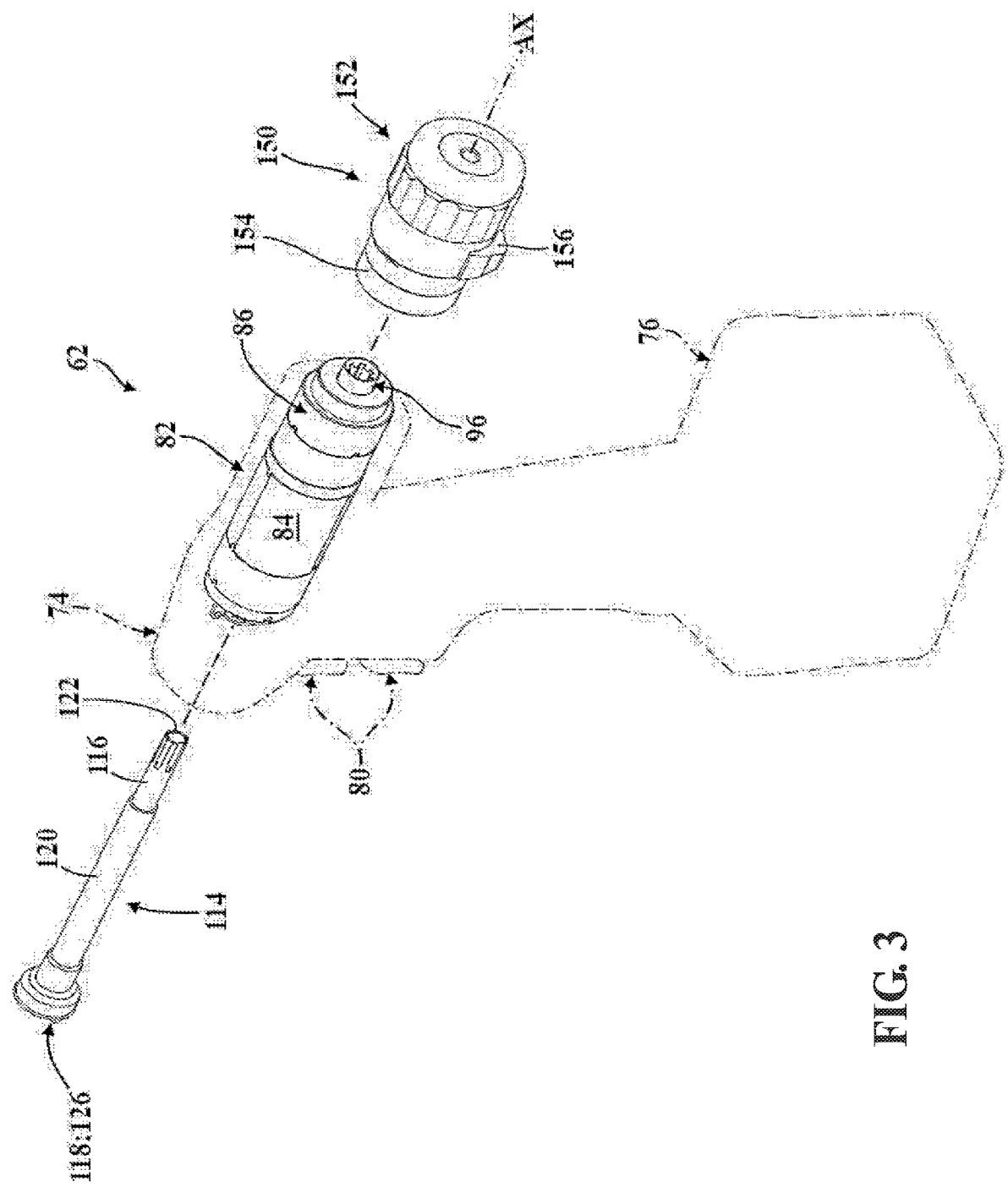
FIG. 3 is a partially-exploded perspective view of portions of the surgical instrument of FIGS. 1-2, shown with the drive assembly and the release mechanism spaced from a phantom outline of the handpiece body to depict an actuator assembly.

In the illustrated configuration, the battery 76 or other power source provides power to a controller 78 (depicted schematically in FIG. 5) which, in turn, is disposed in communication with an input control 80 and an actuator assembly 82 (see also FIG. 3). The input control 80 and the actuator assembly 82 are each supported by the handpiece body 74. The controller 78 is generally configured to facilitate operation of the actuator assembly 82 in response to actuation of the input control 80. The input control 80 has a trigger-style configuration in the illustrated configuration, is responsive to actuation by a user (e.g., a surgeon), and communicates with the controller 78, such as via electrical signals produced by magnets and Hall effect sensors. Thus, when the surgeon actuates the input control 80 to operate the surgical instrument 62, the controller 78 directs power from the battery 76 to the actuator assembly 82 which, in turn, generates rotational torque employed to rotate the drill bit 66, as described in greater detail below. The handpiece body 74, the battery 76, the controller 78, and the input control 80 could each be configured in a number of different ways to facilitate generating rotational torque without departing from the scope of the present disclosure.

Figure 5:
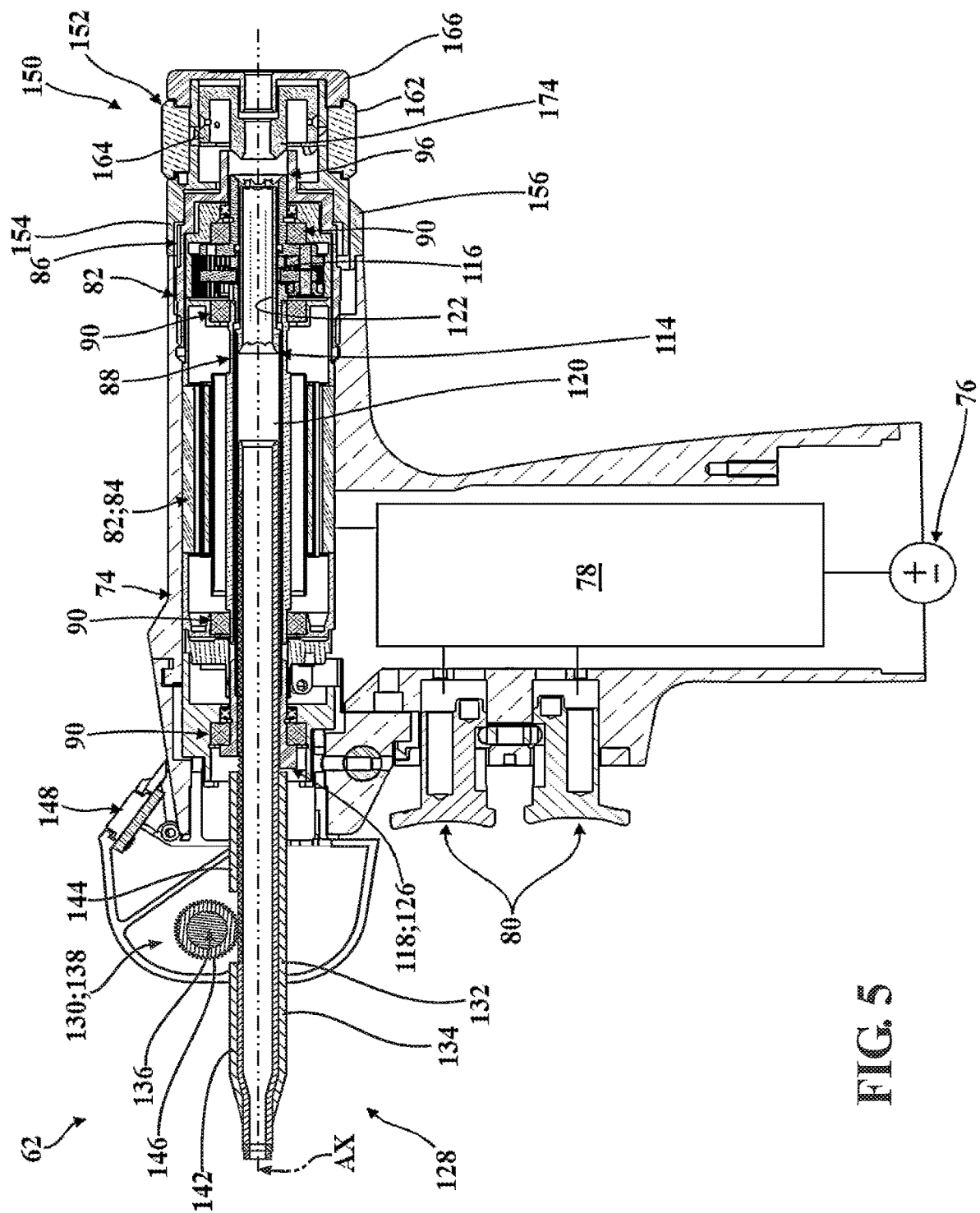
FIG. 5 is a sectional view taken longitudinally through the surgical instrument of FIGS. 1-5, with the end effector assembly removed from the surgical instrument.

As also shown in FIG. 3, the actuator assembly 82 generally comprises an electric motor 84 and a gearset 86 which are each supported within the handpiece body 74. The motor 84 is configured to selectively generate rotational torque in response to commands, signals, and the like received from the controller 78. As is best shown in FIG. 5, the motor 84 comprises a rotor cannula 88 supported for rotation about the axis AX by a pair of bearings 90. A drive gear 92 arranged adjacent to the gearset 86 is coupled to and rotates concurrently with the rotor cannula 88, and is employed to transmit rotational torque to the gearset 86. To this end, in the illustrated configuration, the gearset 86 is realized as two-stage compound planetary arrangement and generally comprises a ring gear housing 94 which, among other things, rotationally supports an output hub 96 via a bearing 90, as well as one or more retaining clips 98, washers 100, and/or seals 102. However, other configurations of the gearset 86 are contemplated.

Further details of the gearset 86 are described, for example, in U.S. patent application Ser. No. 15/887,507, filed on Feb. 2, 2018 and entitled "Drill Bit for Handheld Surgical Instrument, the contents of which are herein incorporated by reference in their entirety, and describe wherein the rotation of the drive gear 92 via actuation of the motor 84 effects concurrent rotation of the output hub 96, and wherein the output hub 96 rotates concurrently with the drill bit 66. The actuator assembly 82 could be configured in other ways without departing from the scope of the present disclosure. By way of non-limiting example, while the illustrated actuator assembly 82 employs a compound planetary arrangement to adjust rotational speed and torque between the drive gear 92 of the motor 84 and the output hub 96, other types of gearsets 86 could be utilized in some configurations. Moreover, while the illustrated actuator assembly 82 employs an electrically-powered brushless DC motor to generate rotational torque, other types of prime movers could be utilized. Other configurations are contemplated.

As noted above, rotational torque generated by the motor 84 effects rotation of the output hub 96 which, in turn, rotates concurrently with the drill bit 66. To this end, and as is best shown in FIGS. 2-5, the surgical instrument 62 further comprises a drive assembly 114 which generally extends through the various cannulated components of the actuator assembly 82 into splined engagement with the output hub 96 of the gearset 86. The drive assembly 114 is configured to facilitate releasable attachment between the drill bit 66 and the surgical instrument 62. The drive assembly 114 generally comprises a driving cannula 116, a driving head 118, and a driving body 120 which extends between, and rotates concurrently with, the driving cannula 116 and the driving head 118. The drive assembly 114 is supported for rotation about the axis AX within the handpiece body 74 via splined engagement with the output hub 96 adjacent the driving cannula 116, and via an arrangement of bearings 90, snap rings 100, and seals 102 adjacent the driving head 118 (see FIG. 6).

Further details of the drive assembly 114 are also described, for example, in U.S. patent application Ser. No. 15/887,507, the contents of which are also herein incorporated by reference in their entirety. In the illustrated configuration, the driving head 118 of the drive assembly 114 comprises a coupling, generally indicated at 126, which is provided to facilitate transmitting rotational torque when the surgical instrument 62 is utilized in connection with other applications besides rotating the drill bit 66 of the present disclosure. More specifically, the illustrated drive assembly 114 is configured such that the surgical instrument 62 can rotate, drive, or otherwise actuate a number of different types of surgical instruments, tools, modules, end effectors, and the like, which can be configured to engage and rotate concurrently with either the bore 122 of the driving cannula 116, or the coupling 126 of the driving head 118. It will be appreciated that this configuration allows the same surgical instrument 62 to be utilized in a broad number of medical and/or surgical procedures. However, it is contemplated that the drive assembly 114 could be configured differently in some configurations, such as to omit a driving head 118 with a coupling 126 in configurations where the surgical instrument 62 configured for dedicated use with the drill bit 66 of the present disclosure.

Referring back to FIGS. 1-3 the illustrated configuration of the surgical instrument 62 further comprises a release mechanism, or coupling mechanism, generally indicated at 150, configured to facilitate removal of the drill bit 66. The coupling mechanism 150 generally comprises a release subassembly 152, a keeper body 154, and a housing adapter 156. The keeper body 154 and the housing adapter 156 are respectively configured to secure the release subassembly 152 to the actuator assembly 82 and the handpiece body 74, and could be realized with a number of different configurations or could be integrated into other parts of the surgical instrument 62 in some configurations.

As noted above, the drill bit 66 of the present disclosure generally extends along the axis AX between the cutting tip portion 70 and the insertion portion 72, and is configured for releasable attachment to the surgical instrument 62 described herein and illustrated throughout the drawings via engagement between the interface 124 of the drill bit 66 and the bore 122 of the driving cannula 116 of the drive assembly 114. The driving cannula 116, in turn, cooperates with the output hub 96 of the gearset 86 of the actuator assembly 82 to facilitate rotating the drill bit 66 about the axis AX.

Referring now to FIG. 2, the drill bit 66 comprises a shank, generally indicated at 176, which extends along the axis AX between a proximal end 178 and a distal end 180. The distal end 180 of the shank 176 is provided with flutes 182 which are helically disposed about the axis AX and extend to the tip of the drill bit 66 to promote workpiece, such as tissue, penetration (see FIG. 2). In the illustrated configuration, the drill bit 66 is also provided with a bearing region 184 coupled to the shank 176 between the proximal end 178 and the distal end 180. The bearing region 184 is sized so as to be received within and rotate relative to the measurement probe 134 of the measurement module 128. Here, the bearing region 184 essentially defines a "stepped" outer region of the shank 176 that affords rotational support along the length of the drill bit 66, and has a larger diameter than adjacent distal and proximal regions of the shank 176 in the illustrated configuration. However, it will be appreciated that the bearing region 184 of the shank 176 of the drill bit 66 could configured in other ways without departing from the scope of the present disclosure. Furthermore, while described as a drill bit 66 in the present disclosure, it is also contemplated that the drill bit 66 could have similar features and be configured as another suitable end effector, or rotary end-effector, such as a bur or reamer.

Figure 4:
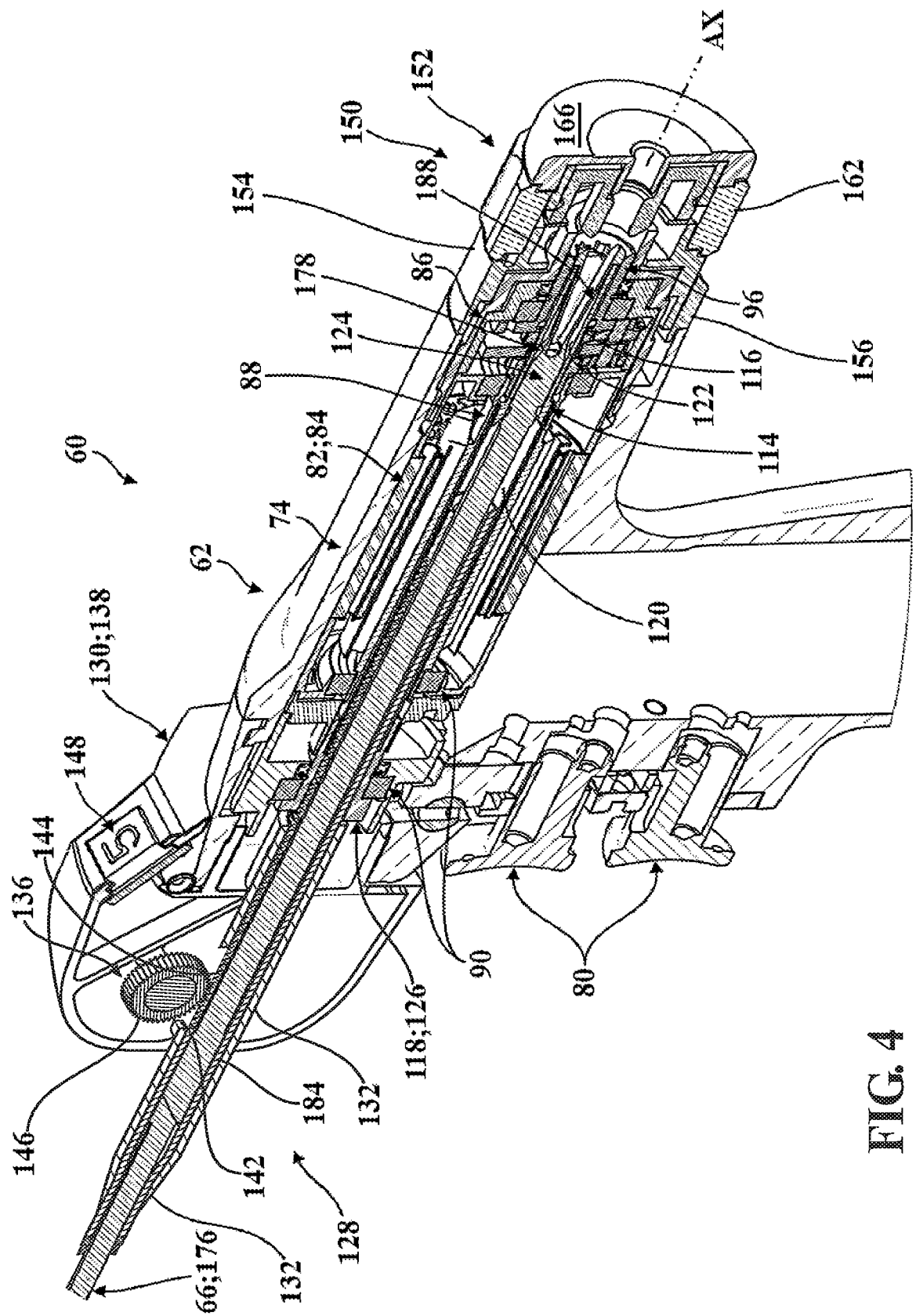
FIG. 4 is a partial isometric sectional view taken along line 4-4 in FIG. 1.

The illustrated configuration of the surgical system 60 further comprises the measurement module, generally indicated at 128, which may be configured to releasably attach to the surgical instrument 62 to provide the surgeon with measurement functionality during use. To this end, and as is best shown in FIGS. 4 and 5, the measurement module 128 may generally comprises a housing 130, a guide bushing 132, a measurement probe 134 (i.e., a probe or a measurement cannula), and a sensor assembly, here a transducer assembly 136. The housing 130 may be releasably attachable to the surgical instrument 62 and generally support the various components of the measurement module 128. The illustrated housing 130 is formed as a pair of housing components 138 which interlock or otherwise attach together, and may be configured for disassembly to facilitate cleaning or servicing the measurement module 128. It should be appreciated that the measurement module may be formed as an integral component of the surgical instrument as well.

In the illustrated configuration, the housing components 138 and the guide bushing 132 comprise correspondingly-shaped features arranged to prevent relative axial and rotational movement therebetween, such as via notches formed in the guide bushing 132 which fit into webs or ribs formed in the housing components 138 (not shown in detail). The guide bushing 132 further comprise a window 142 for use with the transducer assembly 136 as described in detail below.

The measurement probe 134 may be disposed within the guide bushing 132 and is supported for translational movement along the axis AX relative to the handpiece. An elongated recessed slot 143 (partially depicted in FIG. 2) is formed transversely into the measurement probe 134 and extends longitudinally. While not specifically illustrated herein, the elongated recessed slot 143 is shaped and arranged to receive a travel stop element which, in turn, is supported by the housing 130 and likewise extends through an aperture formed transversely through the side of the guide bushing 132; this arrangement serves both to limit how far the measurement probe 134 can be axially extended or retracted relative to the guide bushing 132, and also prevents the measurement probe 134 from rotating about the axis AX. However, it will be appreciated that the measurement module 128 could be configured to limit or prevent movement of the measurement probe 134 in other ways without departing from the scope of the present disclosure.

As illustrated, the measurement probe 134 further comprises rack teeth 144 which are disposed in meshed engagement with a gear 146 of the transducer assembly 136. As shown in FIG. 5, the window 142 of the guide bushing 132 is arranged adjacent to the transducer assembly 136 to facilitate the meshed engagement between the rack teeth 144 and the gear 146. The gear 146 includes a shaft portion 147 extending along a common gear axis CAX. The gear 146 itself is rotatable 360 degrees or more about the common gear axis CAX as the probe 134 moves along the axis AX relative to the housing 130.

The transducer assembly 136 is responsive to rotation of the gear 146 resulting from axial movement of the measurement probe 134 in order to generate electrical signals representing changes in the position of the measurement probe 134 relative to the housing 130 along the axis AX. Thus, it will be appreciated that the transducer assembly 136 is able to provide the surgical instrument 62 with enhanced functionality. By way of example, in some configurations, the transducer assembly 136 may be disposed in communication with the controller 78, which may be configured to interrupt or adjust how the motor 84 is driven based on movement of the measurement probe 134, such as to slow rotation of the drill bit 66 at a specific drilling depth into the workpiece. The transducer assembly 136 may also be disposed in communication with an output device 148, such as a display screen, one or more light-emitting diodes (LEDs), and the like, to provide the surgeon with information relating to movement of the measurement probe 134, such as to display a real-time drilling depth, a recorded historical maximum drilling depth, and the like. Other configurations are contemplated.

The controller 78 comprises one or more microprocessors for processing instructions or for processing algorithms stored in memory to carry out the functions described herein. Additionally or alternatively, the controller 78 may comprise one or more microcontrollers, subcontrollers, field programmable gate arrays, systems on a chip, discrete circuitry, and/or other suitable hardware, software, or firmware that is capable of carrying out the functions described herein. The controller 78 may be carried in the handpiece body 74 as illustrated in FIG. 5, or elsewhere in the surgical system 60, or may be remotely located. Memory may be any memory suitable for storage of data and computer-readable instructions. For example, the memory may be a local memory, an external memory, or a cloud-based memory embodied as random access memory (RAM), non-volatile RAM (NVRAM), flash memory, or any other suitable form of memory.

In certain embodiments, the controller 78 comprises an internal clock to keep track of time. In one embodiment, the internal clock is a microcontroller clock. The microcontroller clock may comprise a crystal resonator; a ceramic resonator; a resistor, capacitor (RC) oscillator; or a silicon oscillator. Examples of other internal clocks other than those disclosed herein are fully contemplated. The internal clock may be implemented in hardware, software, or both. In some embodiments, the memory, microprocessors, and microcontroller clock cooperate to send signals to and operate the various components to meet predetermined timing parameters.

Figure 6:
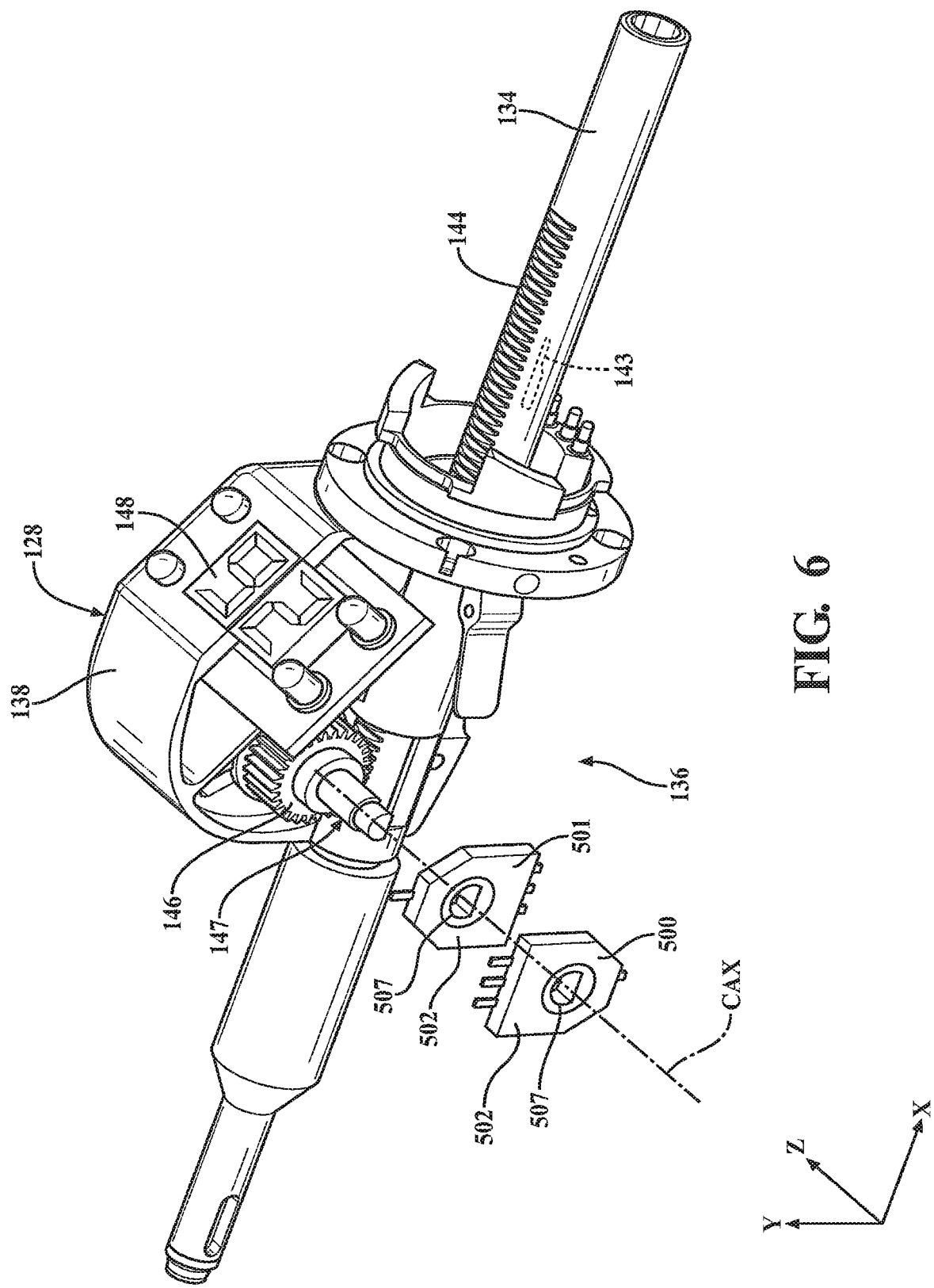
FIG. 6 is a partially-exploded perspective view of the measurement module of FIGS. 1-5.
Figure 7A:
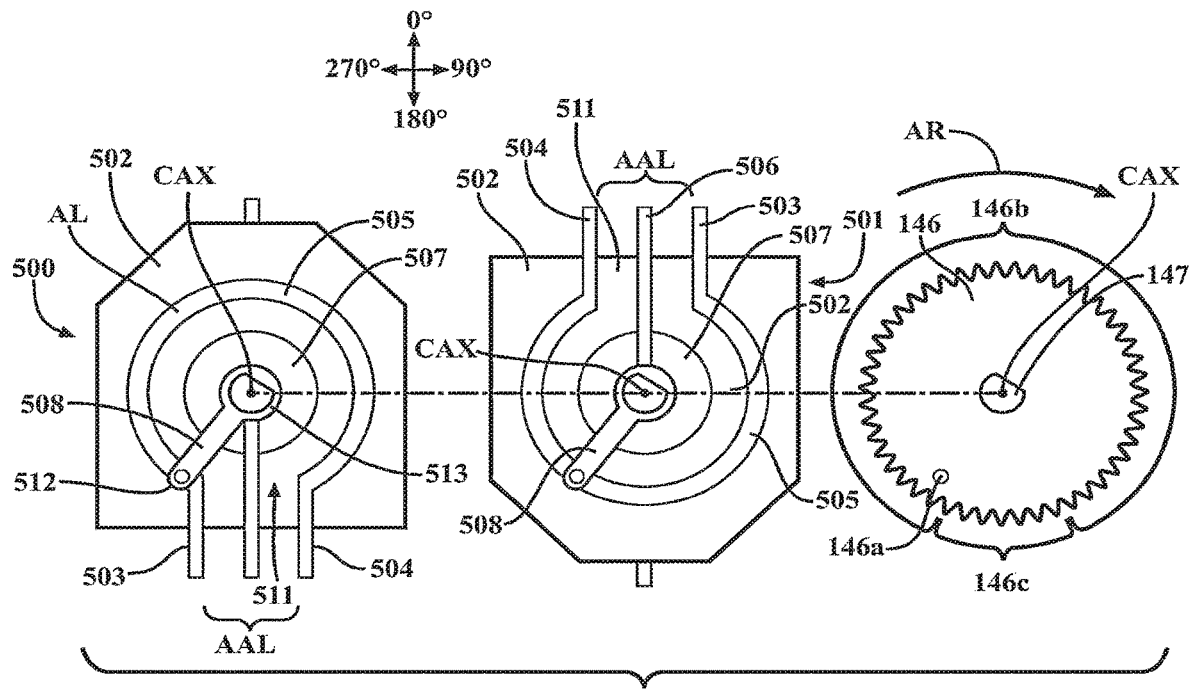
FIGS. 7A-7C is a partially-exploded front perspective view of the gear and the pair of potentiometers of the measurement module, with the potentiometers rotated at 180 degrees with respect to one another, and illustrating various positionings of the wiper arms correlated to a reference point on the gear.
Figure 7B:
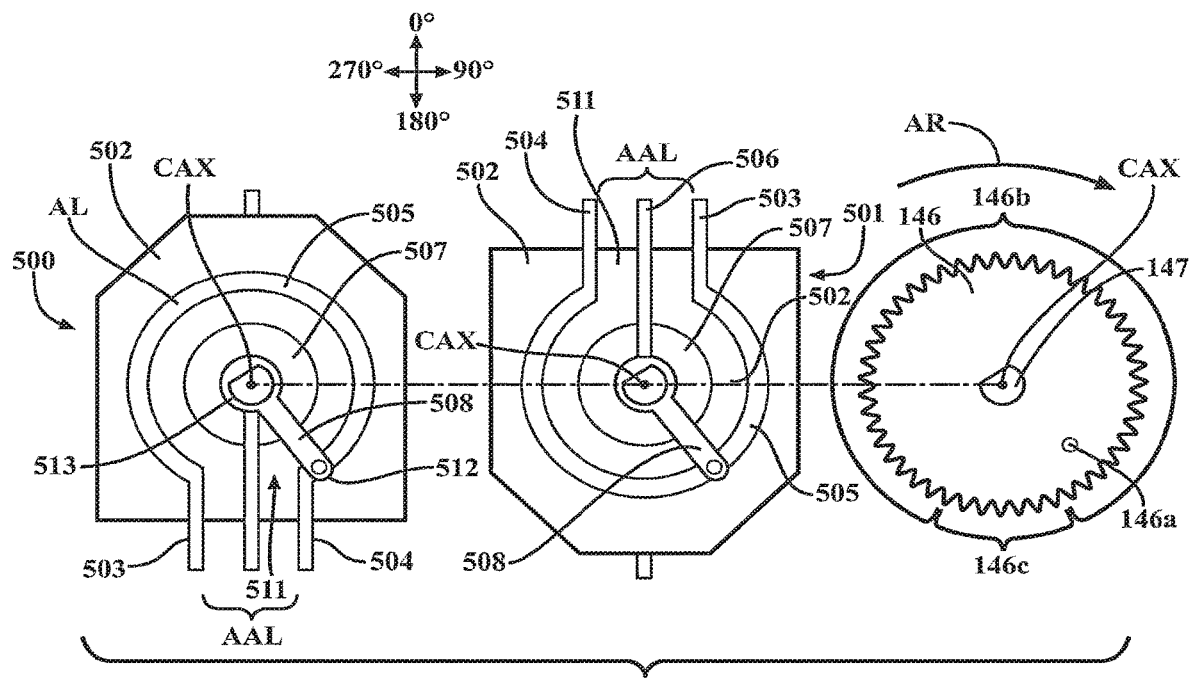
Figure 7C:
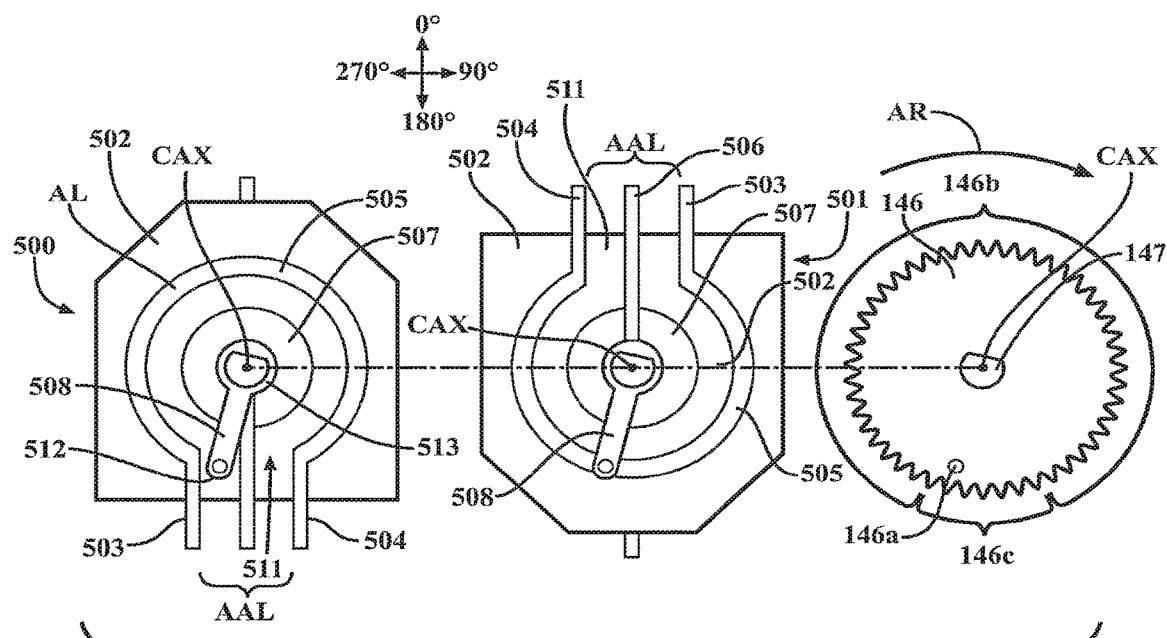
Figure 8:
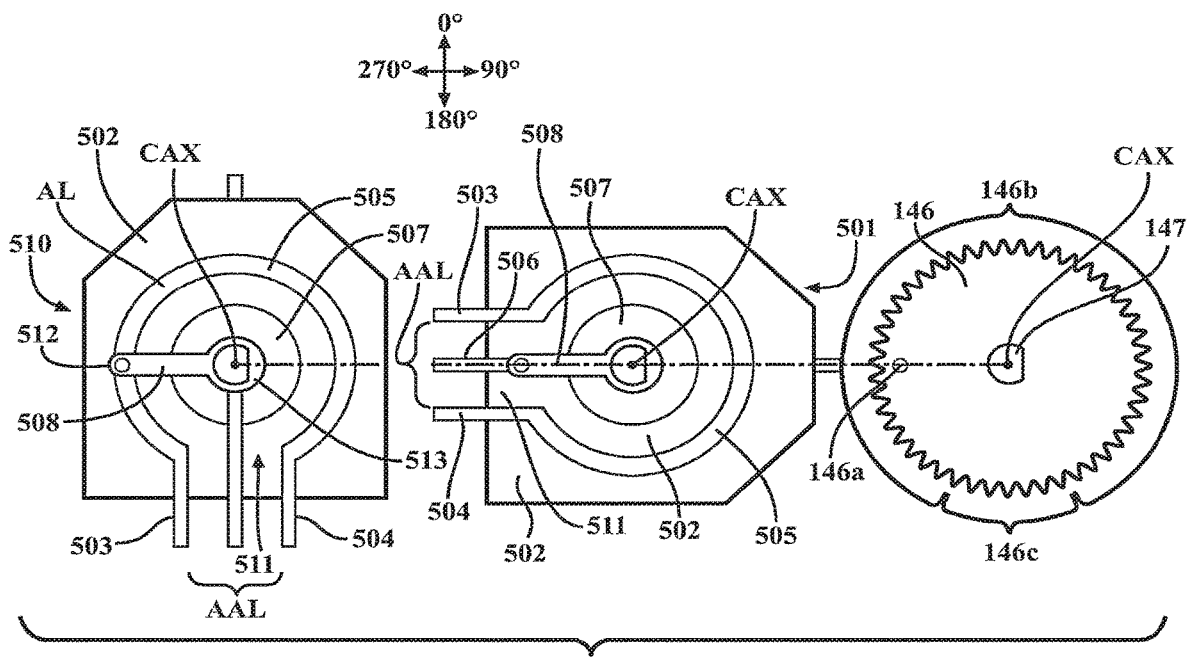
FIG. 8 is a front view of the gear and the pair of potentiometers of the measurement module, with the potentiometers rotated at 90 degrees with respect to one another, and illustrating one positioning of the wiper arms correlated to a reference point on the gear.

In the embodiment described herein, and as best shown in FIGS. 6-8, the transducer assembly 136 includes at least two rotational sensor devices, here shown as a pair of potentiometers 500, 501, which are positioned in proximity to one another within the housing portion 138. For ease of description below, a pair of potentiometers 500, 501 are described hereinafter.

As best shown in FIGS. 7-8, each of the potentiometers 500, 501, which may be the same or different, are rotatable potentiometers and include a body portion 502 and a rotor portion 507 positioned within the body portion 502. The rotor portion 507 of each of the potentiometers 500, 501 is coupled to the gear 146 via the shaft portion 147 and is thus rotatable as the gear 146 rotates about the common gear axis CAX. The body portion 502 is fixedly coupled to the housing portion 138, and thus does not rotate as the rotor portion 507 rotates. The body portion 502, in certain embodiments, is integral with the housing portion 138. In particular, the rotor portions 507 of the potentiometers 500, 501 are rotatable 360 degrees about the common gear axis CAC as the gear 146 rotates. In other words, the potentiometers 500, 501 are of the type that do not include stops (i.e., stop members) that limit the rotation of the rotor portions 507 relative to the body portions 502 to less than 360 degrees of rotation. Stated still another way, the rotor portions 507 are freely rotating with the gear 146.

The body portion 502 includes a pair of terminal portions 503, 504 connected to a resistive element 505. The first terminal portion 503 is connected (i.e., is electrically connected) to a power source, such as the battery 76, and is supplied with a first reference signal (i.e., a predefined voltage) from the power source. The second terminal portion 504 is connected to a second reference signal. In certain embodiments, the second reference signal is a ground. An inner channel (not shown) of the body portion 502 is provided to serve as the void for containing conductors (such as a flex circuit) that extend from the respective terminal portions 503, 504 and 506. The body portion 502 also includes a third terminal portion 506 that is connected (i.e., electrically connected) to the controller 78.

The rotor portion 507 of each of the potentiometers 500, 501 also includes a wiper arm 508 that extends radially outward from the common gear axis CAX, with its radially outward end 512 configured to be connected to (i.e., contact, or electrically connect) the resistive element 505 or to be positioned along the gap 511 depending upon its relative rotational positioning of the wiper arm 508 about the common gear axis CAX with respect to the body portion 502. Another portion of the wiper arm 508, shown here as the radially inward end 513 that terminates at a point corresponding to the common gear axis CAX, is connected (i.e., electrically connected) to the third terminal portion 506. The gear 146 is connected to each one of the respective rotor portions 507 by way of the shaft portion 147. Therefore, the rotation of the gear 146 about the common gear axis CAX results in the like rotation of the wiper arms 508 of the potentiometers 500, 501 about the common gear axis CAX and about the respective static body portions 502.

The resistive element 505 may be arcuate in shape, defining an arcuate length AL between the pair of terminal portions 503, 504, and is positioned along a surface of the body portion 502 between the terminal portions 503, 504. A gap 511 extends along a portion of the body portion 502 between the second terminal portion 504 and the first terminal portion 503 and defines an additional arcuate length AAL that does not include the resistive element 505.

As noted above, the length of the wiper arm 508, corresponding to the radius (r) of the wiper arm 508 from the radially inward end 513 to the radially outward end 512, is configured such that the radially outward end 512 of the wiper arm 508 is connected to the resistive element 505 or is positioned along the gap 511, and as such the arcuate length AL of the resistive element 502 and the additional arcuate length AAL of the gap 511 corresponds to the arc defined by the radially outward end 512 of the wiper arm 508 as it rotates 360 degrees about the common gear axis CAX. The total arcuate length of this arc, which corresponds to the sum of the arcuate length AL and the additional arcuate length AAL, is equal to $2\pi r$, with r defined as the radial length of the wiper arm 508 from the radially outward end 512 to the center of rotation CAX.

In certain embodiments, the arcuate length AL of the resistive element 505 is less than or equal to $11\pi r/6$ (corresponding to less than or equal to 330 degrees of the 360 degrees of rotation of wiper arm 508 in a single rotation of the gear 146), while the corresponding arcuate length AAL corresponding to the gap 511 is greater than or equal to $\pi r/6$ and less than $2\pi r$ (corresponding to the remainder of the 360 degrees of rotation of wiper arm 508 in a single rotation of the gear 146, i.e., greater than or equal to 30 degrees and less than 360 degrees of rotation in a single rotation of the gear 146), with the total length equal to $2\pi r$ as noted above.

When the wiper arm 508 of one or both of the potentiometers 500, 501 is positioned such that it is in contact with the resistive element 505, an output signal is generated from the wiper arm 508 that is sent to the controller 78, with the output signal corresponding to the relative positioning of the wiper arm 508 along the arcuate length AL of the resistive element 505 and scaled with respect to the received first reference signal received by the resistive element from the first terminal portion 503. The scale of the first reference signal received by the controller 78 through the wiper arm 508 and third terminal portion 506, as one of ordinary skill appreciates, is stronger when the wiper arm 508 is positioned nearer to the first terminal portion 103 and is progressively weaker as the wiper arm 508 is rotated to a position nearer to the second terminal portion 504. Conversely, when the wiper arm 508 of one of the potentiometers 500, 501 is positioned within the gap 511, an interrupted signal or no signal is generated from the wiper arm 508 that is sent to the controller 78 (known as the floating position, corresponding to a high ohmic impedance). The generated output signal or signals received by the controller 78, or the interrupted signals, are interpreted by the controller 78 through its stored algorithms to determine the relative positioning of the probe 100 relative to the housing 130, and thus use the information to determine the relative depth of the bore in the workpiece, such as tissue or bone, formed by the drill bit, as will be explained further below.

As also illustrated in FIGS. 6-8, the potentiometers 500, 501 are stacked adjacent to each other in the z-direction in a manner such that the wiper arm 508 of at least one of the pair of potentiometers 500, 501 remains in contact with its respective resistive element 505 at all times, regardless of relative rotational positioning of wiper arms 508 of the pair of potentiometers 500, 501. Accordingly, at all times, at least one generated output signal via the wiper arm 508 in contact with the resistive element 505 is received by the controller 78 that can be used to determine the relative depth of the bore in the workpiece formed by the drill bit, as will be explained further below.

To accomplish this, the body portion 502 of one of the potentiometers 500 is rotately offset about the common gear axis CAX relative to the body portion 502 of the other one of the potentiometers 501 such that the resistive element 505 of the second potentiometer 501 is aligned along at least the entirety of the gap 511 of the first potentiometer 500, when viewed in the z-direction, as in FIGS. 7 and 8. This offset rotational alignment of the resistive elements 505 may be confirmed by comparing their relative alignments of the resistive elements 505, in the z-direction as shown in FIGS. 7 and 8 with a reference point 146a assigned on the circumference of the gear 146 as it rotates 360 degrees around the common gear axis CAX.

The rotation of the body portion 502 of the second potentiometer 501 about the common gear axis CAX relative to the body portion of the body portion 502 of the first potentiometer 500, as illustrated in FIGS. 7 and 8, may be defined in terms of the number of degrees of rotation as it relates to a Cartesian coordinate system. Accordingly, in FIG. 7A-7C, the x-axis in a Cartesian coordinate system is illustrated as right and left, the y-axis in a Cartesian coordinate system is illustrated as up and down, and the z-axis may be defined as into and out of the page. The up position may be designated at 0 degrees, with the down position at 180 degrees, and with the right and left positions at 90 and 270 degrees, respectively. By way of example, the rotation the body portion 502 of the first potentiometer 500 one-hundred eighty degrees about the common gear axis CAX relative to the second potentiometer 501 (or vice versa) and fixing the body portion 502 in that configuration, such as shown in FIGS. 7A-7C, results in the terminal portions 503, 504, 506 of the respective potentiometers 500, 501 being positioned 180 degrees rotationally offset from one another (as shown in FIGS. 7A-7C, the terminal portions 503, 504, 506 of potentiometer 500 are positioned at 180 degrees while the terminal portions 503, 504, 506 of potentiometer 501 are positioned at 0 degrees). By way of a second example, as shown in FIG. 8, rotating the first potentiometer 500 ninety degrees counterclockwise relative to the second potentiometer 501 about the common gear axis CAX, and fixing the body portions 502 in that configuration, results in the terminal portions 503, 504, 506 of the respective potentiometers being positioned 90 degrees rotationally offset from one another (as shown in FIG. 8, the terminal portions 503, 504, 506 of potentiometer 500 are positioned at 0 degrees while the terminal portions 503, 504, 506 of potentiometer 501 are positioned at 90 degrees). It should be appreciated that other rotational offsets of the potentiometers 500, 501 relative to one another about the common gear axis CAX are also contemplated, so long as the offset is sufficient to ensure that at least one wiper arm 508 of at least one of the potentiometers 500, 501 is in contact with its resistive element 505. In certain embodiments, the gap 511 between the terminal portions 503, 504 corresponds to about 30 degrees of rotational offset, and accordingly the rotational offsets may be anywhere from 30 to 330 degrees relative to one another, such as 45 degrees, 60 degrees, 75 degrees, 105 degrees, 120 degrees, 150 degrees, 210 degrees, 270 degrees, etc.

To do the comparison of the rotational offset of the respective elements 505 of the pair of potentiometers 500, 501, the reference point 146a is assigned to a relative position on the gear 146. For ease of description and illustration, as provided in FIGS. 7A, the reference point 146a has been assigned to a position on the gear 146 corresponding to the intersection of the resistive element 505 and the first terminal portion 503 on the first potentiometer 500 when viewed from the z-direction. The gear 146, for illustrative and description purposes, can be subdivided into a first arcuate region 146b and a second arcuate region 146c, which together sum to 360 degrees of rotation (i.e., one full revolution of the gear 146). The first arcuate region 146b corresponds the arcuate length AL of the resistive element 505 of the first potentiometer 500 when viewed in the z-direction, while the second arcuate region 146c corresponds to the additional arcuate length AAL associated with the gap 511 of the first potentiometer when viewed in the z-direction. The first and second arcuate regions 146b, 146c, being static reference regions, do not rotate as the gear 146 and the reference point 146a rotates about the common axis CAX, but maintain fixed coordination with the static arcuate length AL of the resistive element 505 and additional arcuate length AAL of the gap 511 of the first potentiometer 500.

As the gear 146 rotates about the common gear axis CAX in a first rotational direction, the reference point 146a correspondingly rotates along an angular path of rotation AR (i.e., an arcuate path of rotation) about the common gear axis CAX through the first arcuate region 146b and the second arcuate region 146c for every full revolution of the gear 146. As such, depending upon the relative amount of rotation of the gear 146 in the first rotational direction, the reference point 146a is either positioned in the first arcuate region 146b or the second arcuate region 146c at all times as the gear 146 rotates 360 degrees about the common gear axis CAX in the first rotational direction.

Referring first to FIG. 7A, the gear 146 is positioned such that the wiper arm 508 of the first potentiometer 500 is positioned at the intersection of the resistive element 505 and the terminal portion 503. At the same time, the wiper arm 508 of the second potentiometer 501 is positioned on the resistive element 505 at a point between the first and second terminal portion 503, 504. In this position, the reference point 146a is in the first arcuate region 146b of the gear 146, and both wiper arms 508 generate output signals to the controller 78 through the third terminal portion 506 by virtue of their electrical connection to the respective resistive element 505, but wherein the scale of the respective output signals is different (assuming that the first reference signal provided through the first terminal portion 503 of each potentiometer 500, 501 is the same) due to the positioning of the respective wiper arms 508 relative to their first and second terminal portions 503, 504.

In FIG. 7B, the gear 146 has rotated such that the positioning of the wiper arm 508 of the first potentiometer 500 is located at the intersection of the resistive element 505 and the second terminal portion 504 and such that the positioning of the wiper arm 508 of the second potentiometer is nearer to the first terminal portion 503 than in FIG. 7A. In this position, the reference point 146a is still in the first arcuate region 146b of the gear 146 (but at a different relative position than in FIG. 7A), and both wiper arms 508 generate output signals to the controller 78 through the third terminal portion 506 by virtue of their electrical connection to the respective resistive element, but wherein the scale of the respective output signals is different from the respective scales in FIG. 7A.

In FIG. 7C, the gear 146 has rotated such that the positioning of the wiper arm 508 of the first potentiometer 500 is located within the gap 511 and such that the positioning of the wiper arm 508 of the second potentiometer 501 is along the resistive element 505 in a position closer to midway between the first and second terminal portions 503, 504. In this position, the reference point 146a is in the second arcuate region 146c of the gear 146, and only the wiper arm 508 of the second potentiometer 501 generates an output signal to the controller 78 through the third terminal portion 506, but wherein the scale of the respective output signal is different from the respective scales in FIGS. 7A and 7B. Further, the output signal of the first potentiometer 500 is interrupted, because there is no electrical contact between the wiper arm 508 and the resistive element 505, resulting in an open, floating condition giving a high (mega-ohm) impedance. As such, the controller 78 receives only an output signal from the second potentiometer 501 (and either receives an interrupted signal, or no signal, from the first potentiometer 500).

While not illustrated, when the gear 146 is rotated such that the wiper arm 508 of the second potentiometer 501 is within the gap 511 (i.e., between the terminal portions 503, 504 along the top of FIGS. 7A-7C, the wiper arm 508 of the first potentiometer 500 is located approximately midway between the first and second terminal portions 503, 504 along the resistive element 505, and the reference point 146a is positioned in the first arcuate region 146b. Here, the output signal of the second potentiometer 501 is interrupted, because there is no electrical contact between the wiper arm 508 and the resistive element 505. As such, the controller 78 receives only an output signal from the first potentiometer 500 of approximately one-half of the first reference signal provided through the first terminal portion 503 (and either receives an interrupted signal, or no signal, from the second potentiometer 501).

As FIGS. 7A-7C illustrate, at each and every potential reference point 146a position as the gear 146 rotates 360 degrees, at least one of the wiper arms 508 of the respective potentiometers 500, 501 is electrically connected to its respective resistive element 505. Accordingly, at each and every reference point position, a respective output signal is generated and sent to the controller 78 which can be used to determine the relative depth of the bore in the workpiece formed by the drill bit, as will be described further below.

Still further, FIGS. 7A-7C confirm that when the reference point 146a is in the first arcuate region 146b, regardless of its relative position within the first arcuate region 146b, the wiper arm 508 of the first potentiometer 500 is in electrical contact with its respective resistive element 505. Also, FIGS. 7A-7C confirm that when the reference point 146a is in the second arcuate region 146c, regardless of its relative position within the second arcuate region 146c, the wiper arm 508 of the second potentiometer 501 is in electrical contact with its respective resistive element 505. In other words, in the configuration of FIGS. 7A-7C, at least one wiper arm 508 of the respective pair of potentiometers 500, 501 is always in contact with its respective resistive element 505, regardless of the positioning of the reference point 146a in either the first or second arcuate regions 146b, 146c.

In FIG. 8, the body portion 502 of the second potentiometer 501 is rotated 90 degrees relative to the body portion 502 of the first potentiometer 500 (as opposed to 180 degrees as in FIGS. 7A-7C). Similar to the arrangement of FIGS. 7A-7C, the amount of rotation of the second potentiometer 501 relative to the first potentiometer 500 is sufficient to ensure that the gap 511 of the second potentiometer 501 is not aligned with the gap 511 of the first potentiometer 500.

Accordingly, as illustrated in the embodiments herein, in order to accomplish this stacking effect with the rotationally offset resistive elements 505, the potentiometers 500, 501 are coupled to the gear shaft 147 such that their body portions 502 are coupled to the housing portion 138 are rotationally offset sufficiently to ensure that the gap 511 of the second potentiometer 501 is not aligned with the gap 511 of the first potentiometer 500. In other words, if the arcuate length AL of the resistive element 505 of each of the first and second potentiometers 500, 501 is $11\pi r/6$ (and hence the gap 511 is $\pi r/6$), the rotated positioning of the body portion 502 of the second potentiometer 501 between 30 and 330 degrees (which correlates to between $\pi r/6$ and $11\pi r/6$) about the common gear axis CAX ensures that gaps 511 of the first and second potentiometers 500, 501 do not overlap when another when viewed from the z-direction.

Stated another way, while FIGS. 7 and 8 illustrate the body portions 502 of the pair of potentiometers 500, 501, rotated at 180 and 90 degrees offset from one another, other rotational offsets of the potentiometers 500, 501 are contemplated. Specifically, the body portions 502 of the pair of potentiometers 500, 501 may be offset from 30 to 330 degrees about the common gear axis CAX, and fixing the body portions 502 in that configuration, which ensures that at least one of the wiper arms 508 (rotating in coordination with one another) is contacting its respective resistive element 505 at all relative positions of the reference point 146a of the gear 146. In other words, through the use of two paired potentiometers 500, 501 as described above, represented in two embodiments in FIGS. 7 and 8, at least one of the pair of potentiometers 500, 501 will be in the non-floating condition at all times, regardless of the rotational positioning of the wiper arms 508 of the potentiometers 500, 501, and thus is capable of providing a valid reading that can be used by the controller 78 to determine the bore depth as can be determined according to the method described below. It is of course possible to use three or more potentiometers in this manner as well.

Figure 9:
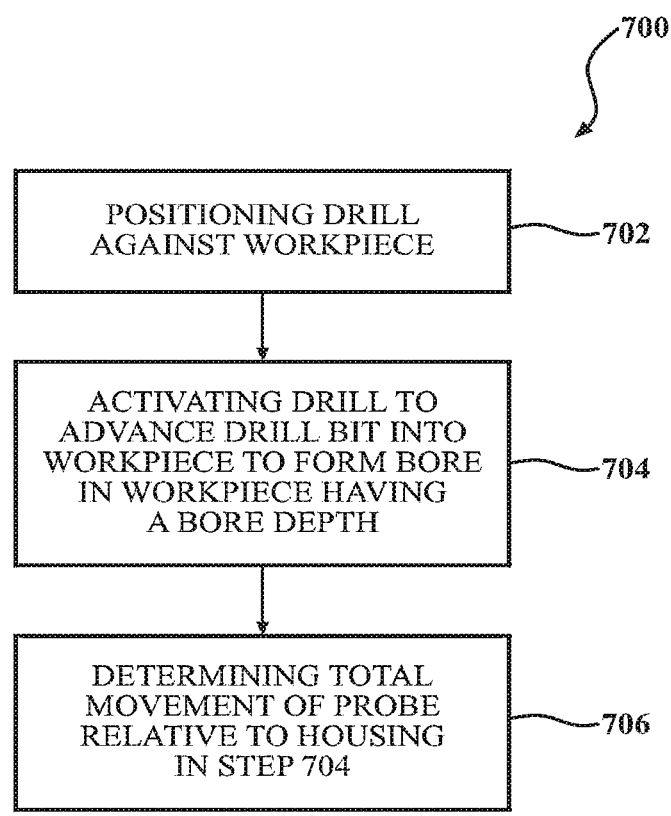
FIG. 9 is a logic flow diagram describing a method in for determining a bore depth in a workpiece formed by a drill bit attached to the surgical drill of FIGS. 1-8.
Figure 10:
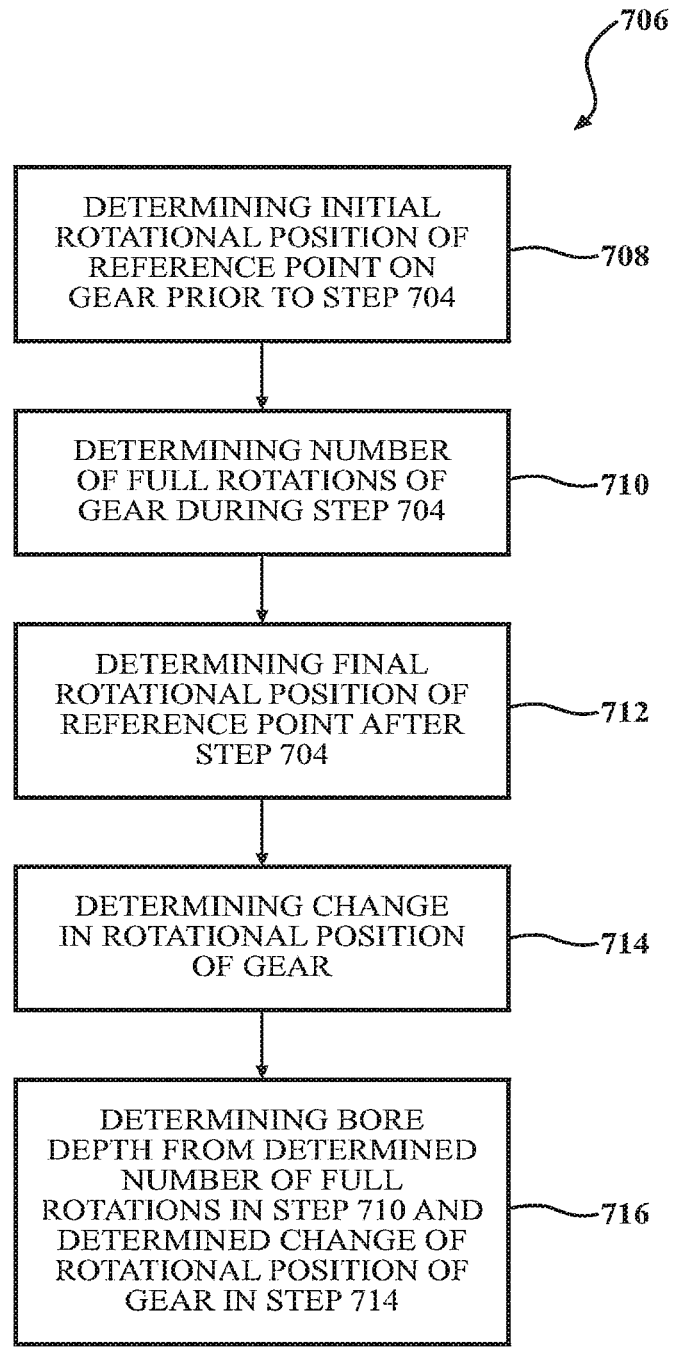
FIG. 10 is a logic flow diagram for Step 706 of the logic flow diagram of FIG. 9.

Referring next to FIGS. 9 and 10, a method for determining a bore depth in a workpiece formed by a drill bit 66 in the drill 60 as described above is also provided. In general, as illustrated in FIG. 9, the logic 700 for determining the bore depth includes three basic steps. First, in Step 702, the drill 60 is positioned against the workpiece. In particular, the drill 60 is positioned such that the cutting tip portion 70 at distal end 180 of the drill bit 66 is placed against the workpiece. Next, in Step 704, the drill 60 is actuated to advance the cutting tip portion 70 of the drill bit 66 into the workpiece to form a bore, or hole, having a bore depth. As a part of Step 704, the controller 78 directs the power source to send a first reference signal (typically in the form of a reference voltage), through the first terminal portion 503 to each of the respective resistive elements 505 of the potentiometers 500, 501. Finally, in Step 706, the bore depth is determined via the controller 78 by determining the total amount of movement of the probe relative to the housing during Step 704. Step 706 can be determined after completion of the drilling of the hole, by the drill 60, or can be determined at any point in time as the hole is being drilled, with the instantaneous bore depth being determined and continuously updated.

In FIG. 10, the details of the logic of Step 706 are described in further detail. First in Step 708, the controller 78 determines the initial, or first, rotational position of the reference point 146a of the gear 146, in certain cases, prior to said step of actuating the drill 60. In particular, the initial rotational position of the reference point 146a of the gear 146 can be determined based upon the respective positioning of the at least two wiper arms 508 as the drill 60 is positioned against the workpiece in Step 702 prior to the actuation of the drill 60 in Step 704. In this position, an initial respective signal(s) is generated from at least one of the at least two wiper arms 508, with each signal scaled to their respective positioning on the resistive element 505 as a function of the respective provided first reference signal. The controller 78 receives the initial respective signal(s) and determines the initial respective position of the reference point 146a of the gear 146 on the basis of the received initial respective signal(s). To aid in determining the initial respective position of the reference point, the memory of the controller 78 includes stored information regarding the size of the gear 146 and includes a pre-stored algorithm that can interpret the scale of the received initial inputs signal(s) and identify the relative positioning of the reference point 146a of the gear 146 corresponding to the scale of the received initial inputs signal(s).

In Step 710, the controller 78 determines a number of full rotations of the gear 146 in a single rotational direction about the common gear axis CAX with the at least two potentiometers 500, 501 during, or after, said step of actuating the drill.

More specifically, the controller 78 determines a number of distinct interrupted signals generated from the wiper arm 508 of one, or both, of the potentiometers 500, 501 during Step 710. Each interrupted signal occurs when the gear 146 is rotated in the single rotational direction such that the reference point 146a of the gear 146 is within the second arcuate region 146c such that the wiper arm 508 of a designated one or both of the potentiometers 500, 501 (typically the first potentiometer 500) is within the gap 511. The end of one interrupted signal occurs when the gear 146 is further rotated in the single rotational direction such that the wiper arm 508 initiates contact with the resistive element 505 at the location corresponding to the first terminal portion 503, or the second terminal portion 504, depending upon which direction the wiper arm 508 is rotating about the common gear axis CAX.

In Step 712, the controller 78 determines a final, or second, rotational position of the reference point 146a of the gear 146 after Step 704 or at any point during step 704. In particular, the final rotational position of the reference point 146a of the gear 146 can be determined based upon the respective positioning of the at least two wiper arms 508 after the actuation of the drill is terminated. In this position, a final, second respective signal is generated from at least one of the at least two wiper arms 508, with each signal scaled to their respective positioning on the resistive element 505 as a function of the respective provided first reference signal. The controller 78 receives the final, second respective signal(s) and utilizes the algorithm stored in the memory of the controller 78 to determine the final respective position of the reference point 146a of the gear 146 on the basis of the received final, second respective signal(s).

In Step 714, the controller 78 determines a change in the rotational position of the reference point 146a of the gear 146 between said determined initial, first rotational position of Step 710 and said determined, second final rotational position of Step 712. More specifically, the controller 78 compares the received initial, first respective signal(s) and the received final, second respective signal(s) and calculates the change in positioning based on the compared signals utilizing an algorithm stored in the memory of the controller 78.

Finally, in Step 716, the controller 78 determines the bore depth from the determined number of full rotations of the gear 146 occurring during Step 712 and from the determined change in the rotational position of the reference point 146a of the gear 146 in Step 714. More specifically, the controller 78 utilizes an algorithm stored in its memory that calculates the relative amount of movement of the probe 100 relative to the housing 130 on the basis of the determined number of interrupted signals and on the determined change in the rotational position of the reference point 146a of the gear 146 and further calculates the bore depth on the basis of the determined relative amount of movement. As a part of Step 716, the controller 78 may send an output signal to the display 148, which provides a reading on the display corresponding to the bore depth that is visible by the operator of the drill 60.

In each of the Steps for the logic 700 of FIG. 10, the controller 78 may be configured to determine the initial, first and final, second positioning of the reference point 146a of the gear 146 on the basis of any single one received initial respective signal, and any single one received final respective signal, or on the basis of both received initial respective signals or both received final respective signals (i.e., based on the combined received initial respective signals or combined received final respective signals, when both of the wiper arms 508 are in contact with the respective resistive elements 505 corresponding to the initial and final respective position of the reference point 146a), to determine the initial and final positioning of the reference point 146a of the gear 146.

In still further embodiments, the controller 78 is configured to configured to continually process generated signals from received from each of the potentiometers 500, 501 during Step 710 to continually determine the respective positioning of the reference point 146a of the gear 146. In this regard, the controller 78 may utilize the received signal from one of the potentiometers 500 or 501 as the primary signal to continually determine the relative positioning of the reference point 146a of the gear 146, and only utilizing the signal received from the second one of the potentiometers 500 or 501 when the primary signal is in the interrupted state (i.e., where the wiper arm 508 of the designated one of the potentiometers 500 or 511 is positioned within the gap 511).

Still further, the controller 78 may be configured to determine the number of complete revolutions of the gear 146 on the basis of the number of interrupted signals from a respective one of the potentiometers 500 or 501, or on the basis of the number of interrupted signals from both of the potentiometers 500, 501.

In further embodiments, as opposed to having a pair of potentiometers 500, 501 stacked in the z-direction as illustrated in FIGS. 7 and 8, the potentiometers 500, 501, could be positioned side-to-side in the x-direction. For example, an additional gear (not shown) could be meshed with the gear 146. A gear shaft from the additional gear could then be coupled to the rotor portion 307 of the second potentiometer 501. The rotation of the gear 146 would in turn rotate the additional gear, and both wiper arms 508 of the first and second potentiometers 500, 501 would rotate as described above. In a manner similar to the embodiments of FIGS. 7 and 8 above, by positioning the body portion 502 of the second potentiometer 501 such that at least one of the wiper arms 508 is always in contact with its respective resistive element 505

The surgical system 60 described herein provides a method for accurately measuring the bore depth in a workpiece formed by the drill bit 66 of the drill while also addressing the deficiencies with surgical drills utilizing a single potentiometer. Specifically, by utilizing at least two potentiometers which are configured such that at least one of the wiper arms is in contact with its respective resistive element regardless of the positioning of the reference point of the gear, the floating condition can be avoided. Still further, the inclusion of the at least one additional potentiometer makes it unnecessary to increase the diameter of the gear size to ensure that the gear, and the coupled single turn potentiometer, do not turn such that the wiper arm is positioned within the gap. This overcomes the further deficiencies of surgical drills having a single potentiometer in terms of undesirable bulk to the drill and potential obstruction of the surgeon's field of vision during the drilling operation.

It should be appreciated that the system described herein may be used for non-surgical applications, such as through drilling through workpieces other than tissue, such as wood, metal, or plastic. Additionally, it should be appreciated that the system may be used in conjunction with end-effectors other than drill bits.

Several configurations have been discussed in the foregoing description. However, the configurations discussed herein are not intended to be exhaustive or limit the disclosure to any particular form. Other configurations are specifically contemplated. For example, while the use of at least two potentiometers in the transducer assembly are described herein in which the first of potentiometers is incapable of detecting a reference point in the second arcuate region of the gear is described above but wherein the second potentiometer does detect the reference point in the second arcuate region, it is contemplated additional potentiometers, and not a single pair of potentiometers, may be utilized such that at least one potentiometer is able to detect a rotational position of the reference point of the gear at all positions within the first and second arcuate regions. Moreover, while the potentiometers or rotational sensor devices described above are typically of the same design, potentiometers or rotational sensor devices of different types or sizes may be utilized. Still further, other types of sensor devices located on the surgical drill, such as Hall sensors or the like, may be utilized in conjunction with the rotational sensors described herein that could provide enhanced precision for measurement. Even still further, it is contemplated that separate gears could be independently coupled to the probe, with each of the separate gears coupled to one, or more than one, potentiometer, and configured to ensure precise measurement of the bore depth and each possible probe position relative to the housing in accordance with the configuration of rotational sensor devices as described above. Still further, while the configurations for the transducer assemblies described above are specifically illustrated with respect to a removable measurement module, it is contemplated that the transducer assembly including the gear and sensor device may be included on a non-removable portion of the surgical drill.

The terminology which has been used is intended to be in the nature of words of description rather than of limitation. Many modifications and variations are possible in light of the above teachings and the disclosure may be practiced otherwise than as specifically described.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

The disclosure is intended to be defined in the independent claims, with specific features laid out in the dependent claims, wherein the subject-matter of a claim dependent from one independent claim can also be implemented in connection with another independent claim.

The present disclosure also comprises the following clauses, with specific features laid out in dependent clauses that may specifically be implemented as described in greater detail with reference to the configurations and drawings above.

I. A measurement module configured for releasable attachment to a surgical instrument, said measurement module comprising:
  a housing;
  a measurement cannula;
  a transducer assembly including a gear coupled to said measurement cannula and configured to rotate more than 360 degrees about a gear axis upon the movement of said probe relative to said housing, said gear having a reference point having an angular path of rotation about said gear axis being divided into a first arcuate region and a second arcuate region, said first arcuate region being separate from said second arcuate region; and
  a transducer comprising at least two potentiometers, each of said at least two potentiometers coupled to said gear,
  a first of said at least two potentiometers configured to detect a rotational position of said reference point in said first arcuate region and a second of said at least two potentiometers configured to detect said rotational position of said reference point in at least said second arcuate region, said first rotational sensor being incapable of detecting said reference point in the second arcuate region.

II. A measurement module configured for releasable attachment to a surgical instrument, said measurement module comprising:
  a housing;
  a measurement cannula;
  a transducer assembly including:
  a gear coupled to said measurement cannula and configured to rotate more than 360 degrees about a gear axis upon the movement of said measurement cannula relative to said housing, said gear having a reference point having an angular path of rotation about said gear axis being divided into a first arcuate region and a second arcuate region, said first arcuate region being separate from said second arcuate region; and
  a transducer comprising at least two rotational sensor devices, each of said at least two rotational sensor devicess fixed rotationally relative to said gear,
  a first rotational sensor device configured to detect a rotational position of said reference point in said first arcuate region and a second rotational sensor device configured to detect said rotational position of said reference point in said second arcuate region, said first rotational sensor device being incapable of detecting said reference point in the second arcuate region, said at least two rotational sensor devices each being adapted for independently generating a output signal corresponding to said detected rotational position of said reference point in said respective first and second arcuate region:
  a controller configured to receive each of said independently generated output signals and, based on each of said independently generated output signals, determine the depth of the bore in the tissue formed by the drill bit.

III. A transducer assembly for use with a surgical tool having a probe and a housing, said transducer assembly comprising:
  a gear coupled to the probe and configured to rotate more than 360 degrees about a gear axis upon the movement of the probe relative to the housing, said gear having a reference point having an angular path of rotation about said gear axis being divided into a first arcuate region and a second arcuate region, said first arcuate region being separate from said second arcuate region; and
  a transducer comprising at least two potentiometers, each of said at least two potentiometers coupled to said gear,
  a first of said at least two potentiometers configured to detect a rotational position of said reference point in said first arcuate region and a second of said at least two potentiometers configured to detect said rotational position of said reference point in at least said second arcuate region, said first potentiometer being incapable of detecting said reference point in the second arcuate region.

What is claimed is:

1. A surgical drill for actuating a drill bit, the surgical drill including:
  a housing;
  a probe moveably mounted to the housing and adapted for placement against a workpiece; and
  a transducer assembly including:
  a gear coupled to the probe and configured to rotate more than 360 degrees about a gear axis upon movement of the probe relative to the housing; and
  a transducer comprising at least two potentiometers, each of the at least two potentiometers coupled to the gear.

2. The surgical drill of claim 1, further comprising a controller configured to receive output signals independently generated by the at least two potentiometers and, based on the independently generated output signals, determine a depth of a bore in tissue formed by a drill bit.

3. The surgical drill of claim 2, further comprising a display, wherein the controller is configured to generate a bore depth signal that is received by the display corresponding to the determined depth of the bore, with the bore depth signal being presented on the display for viewing by a user.

4. The surgical drill of claim 2, wherein each one of the at least two potentiometers comprises:
  a body portion having a pair of terminal portions electrically connected to a resistive element, with one of the pair of terminal portions configured to receive a first reference signal and another one of the pair of terminal portions connected to a second reference signal, the resistive element having an arcuate shape defining an arcuate length between the pair of terminal portions, the pair of terminal portions separated by a gap defining an additional arcuate length, and a rotor portion coupled within the body portion and coupled to the gear, the rotor portion including a wiper arm electrically connected to a third terminal portion of the body portion, wherein the rotation of the gear about the gear axis causes the wiper arms to rotate about the gear axis, wherein a positioning of the wiper arm along the arcuate length of the resistive element generates an output signal at the third terminal portion, with the output signal corresponding to a relative positioning along the arcuate length of the resistive element and scaled with respect to the first reference signal, and wherein a positioning of the wiper arm within the gap generates an interrupted signal, and wherein the wiper arm is positioned so as to connect to the resistive element along the arcuate length corresponding to rotational positions of the gear as the gear rotates 360 degrees about the gear axis.

5. The surgical drill of claim 4, wherein the arcuate length of the resistive element on the body portion of each of the potentiometers is less than or equal to $11\pi r/6$, wherein r is a radial length of each respective one of the wiper arms.

6. The surgical drill of claim 4, wherein the body portion of one of the at least two potentiometers is rotated about the gear axis from greater than 0 degrees to less than 360 degrees relative to the body portion of another one of the at least two potentiometers.

7. The surgical drill of claim 4, wherein each wiper arm of the at least two potentiometers is positioned so as to be electrically connected with its respective resistive element at least one rotational position of the gear.

8. The surgical drill of claim 4, wherein each wiper arm of the at least two potentiometers is positioned so as to be electrically connected with its respective resistive element at least one rotational position of the gear, wherein each wiper arm of the at least two potentiometers generates a respective output signal corresponding to its relative positioning along the arcuate length of its respective resistive element and scaled with respect to the received first reference signal, and wherein the controller is configured to receive and combine the output signals from each wiper arm of the at least two potentiometers and, based on the output signals, determine an amount of movement of the probe relative to the housing.

9. The surgical drill of claim 8, wherein each of the wiper arms generates a respective output signal corresponding to its relative positioning along the arcuate length of its respective resistive element and corresponding to the received first reference signal, and wherein the controller is configured to receive the output signals and, based on the output signals, determine an amount of movement of the probe relative to the housing.

10. The surgical drill of claim 4, wherein when the wiper arm of a single one of the at least two potentiometers is positioned so as to be connected with its respective resistive element, the controller is configured to receive the generated corresponding output voltage signal from the single one of the at least two potentiometers and, based on the generated corresponding output signal, determine an amount of movement of the probe relative to the housing.

11. The surgical drill of claim 4, wherein the controller is further configured to determine a number of full revolutions of the gear rotating about the gear axis, with each full revolution corresponding to a predefined amount of movement of the probe relative to the housing, and, based on each of the output signals and each of the interrupted signals and the number of full revolutions, determine a total amount of movement of the probe relative to the housing.

12. A surgical tool including:
a housing;
a probe moveably mounted to the housing; and
a transducer assembly including:
a gear coupled to the probe and configured to rotate more than 360 degrees about a gear axis upon movement of the probe relative to the housing;
at least two rotational sensor devices, each of the at least two rotational sensor devices fixed rotationally relative to the gear, and the at least two rotational sensor devices each being adapted for independently generating an output signal; and
a controller configured to receive output signals independently generated by the at least two rotational sensor devices and, based on each of the independently generated output signals, determine a depth of a bore formed in tissue.

13. The surgical tool of claim 12, wherein the controller is further configured to:
determine a first rotational position of the gear;
determine a number of full rotations of the gear in a single rotational direction about a gear axis from the determined first rotational position, with each of the full rotations corresponding to a predefined amount of movement of the probe relative to the housing;
determine a second rotational position of the gear; and
determining an amount of movement of the probe relative to the housing based on the first and second rotational positions and the number of full rotations of the gear.

14. The surgical tool of claim 12, further comprising a display, wherein the controller is configured to generate a bore depth signal that is received by the display corresponding to the determined depth of the bore, with the bore depth signal being presented on the display for viewing by a user.

15. A method for determining a bore depth in a workpiece formed by a drill bit attached to a drill, the drill including a housing, a probe coupled to the housing, and a transducer assembly including a gear and a transducer including at least two rotational sensor devices, the method comprising:
determining a first rotational position of the gear;
determining a number of full rotations of the gear in a single rotational direction about a gear axis from the determined first rotational position, with each of the full rotations corresponding to a predefined amount of movement of the probe relative to the housing;
determining a second rotational position of the gear; and
determining an amount of movement of the probe relative to the housing from the first and second rotational positions and the number of full rotations of the gear.

16. The method of claim 15, wherein the second rotational position of the gear is different than the first rotational position.

17. The method of claim 15, wherein the drill also includes a controller coupled to the transducer assembly, and wherein the method further comprises the step of generating a bore depth signal from the controller corresponding to the amount of movement of the probe relative to the housing.

18. The method of claim 17, wherein the drill further comprises a display coupled to the controller, and wherein the method further comprises displaying the generated bore depth signal on the display.

19. The method of claim 17, wherein each of the at least two rotational sensor devices comprises a potentiometer, with each potentiometer comprising:
- a body portion having a pair of terminal portions electrically connected to a resistive element, with one of the pair of terminal portions configured to receive a first reference signal and another one of the pair of terminal portions connected to a second reference signal, the resistive element having an arcuate shape defining an arcuate length between the pair of terminal portions, the pair of terminal portions separated by a gap defining an additional arcuate length, and
- a rotor portion coupled within the body portion and coupled to the gear, the rotor portion including a wiper arm electrically connected to a third terminal portion of the body portion, wherein the rotation of the gear about the gear axis causes the wiper arms to rotate about the gear axis,
- wherein a positioning of the wiper arm along the arcuate length of the resistive element generates an output signal at the third terminal portion, with the output signal corresponding to a relative positioning along the arcuate length of the resistive element and scaled with respect to the first reference signal, and
- wherein a positioning of the wiper arm within the gap generates an interrupted signal, and
- wherein the wiper arm is positioned so as to connect to the resistive element along the arcuate length corresponding to rotational positions of the gear as the gear rotates 360 degrees about the gear axis.

20. The method of claim 19, wherein the step of determining an amount of movement of the probe relative to the housing comprises:
- providing the first reference signal to the one of the pair of terminal portions;
- generating an initial respective signal from each of the wiper arms corresponding to an initial rotational position of the gear after the drill is positioned against the workpiece and prior to a step of actuating the drill;
- sending each of the generated initial respective signals to the controller;
- determining a final positioning of each of the wiper arms corresponding to a final rotational position of the gear after the step of actuating the drill;
- generating a final respective signal from each of the wiper arms corresponding to the determined final respective positioning of each of the wiper arms after the step of actuating the drill;
- determining a number of distinct interrupted signals generated from a single one of the wiper arms during the step of actuating the drill;
- generating and sending an additional signal to the controller corresponding to the determined number of distinct interrupted signals;
- processing each of the initial respective signals, each of the final respective signals, and the additional signal with the controller; and
- generating a bore depth signal from the controller corresponding to the initial respective signals, the final respective signals, and the additional signal.

\* \* \* \* \*